(12) United States Patent
Gebauer et al.

(10) Patent No.: US 11,643,627 B2
(45) Date of Patent: May 9, 2023

(54) HOUSING FOR HOLDING A FLEXIBLE BIOPROCESS BAG

(71) Applicant: CYTIVA SWEDEN AB, Uppsala (SE)

(72) Inventors: Klaus Gebauer, Uppsala (SE); Nagaraj Raghavendra Rao, Bangalore (IN); Anindya Kanti De, Bangalore (IN); Anindya Sengupta, Bangalore (IN); Mats Olsson, Uppsala (SE); Colin R. Tuohey, Marlborough, MA (US); Jonathan A. Kenney, Marlborough, MA (US); Richard Lee Damren, Marlborough, MA (US); Ralph Stankowski, Westborough, MA (US); Nirmal Kumar Thanikachalam, Bangalore (IN)

(73) Assignee: CYTIVA SWEDEN AB, Uppsala (SE)

( * ) Notice: Subject to any disclaimer, the term of this patent is extended or adjusted under 35 U.S.C. 154(b) by 292 days.

(21) Appl. No.: 16/474,626

(22) PCT Filed: Dec. 27, 2017

(86) PCT No.: PCT/EP2017/084621
§ 371 (c)(1),
(2) Date: Jun. 28, 2019

(87) PCT Pub. No.: WO2018/122247
PCT Pub. Date: Jul. 5, 2018

(65) Prior Publication Data
US 2019/0322970 A1    Oct. 24, 2019

(30) Foreign Application Priority Data

Dec. 29, 2016  (IN) .............................. 201611044877
Dec. 29, 2016  (IN) .............................. 201611044898
Mar. 30, 2017  (IN) .............................. 201741011286

(51) Int. Cl.
C12M 1/00       (2006.01)
C12M 3/00       (2006.01)

(52) U.S. Cl.
CPC ............ C12M 23/14 (2013.01); C12M 23/26 (2013.01); C12M 23/28 (2013.01); *C12M 23/48* (2013.01)

(58) Field of Classification Search
None
See application file for complete search history.

(56) References Cited

U.S. PATENT DOCUMENTS 7,819,934 B2 * 10/2010  Galliher ................. C12M 41/00
                                                                 454/192
2006/0280028 A1 * 12/2006  West ..................... B01F 27/213
                                                                 366/331
(Continued)

FOREIGN PATENT DOCUMENTS

CN        103930196       7/2014
WO      2009132192 A2    10/2009
(Continued)

OTHER PUBLICATIONS

English Translation of Chinese Office Action dated Jun. 22, 2022 from corresponding Chinese Application No. 201780087578.7.

*Primary Examiner* — Donald R Spamer
*Assistant Examiner* — Nathan G Esperon
(74) *Attorney, Agent, or Firm* — Grogan, Tuccillo & Vanderleeden, LLP

(57) ABSTRACT

A support housing for a flexible bioprocess bag, the housing comprising at least one side wall having a first segment and a second segment, the first segment movable in relation to the second segment between an open and a closed position, wherein at least a supporting part of the housing is translatable from an operating position to a bag loading position, wherein the supporting part comprises one or more retainers (Continued)

a)

b)

for holding the flexible bioprocess bag upon re-translation of the supporting part to the operating position and movement of the first segment to the closed position, and wherein the first segment comprises a first drive unit for connecting and driving a first mixing unit in the flexible bioprocess bag.

26 Claims, 24 Drawing Sheets

(56) References Cited

U.S. PATENT DOCUMENTS

| | | | |
|---|---|---|---|
| 2009/0269849 A1 | 10/2009 | Lee et al. | |
| 2010/0055764 A1* | 3/2010 | Martin | C12M 23/14 435/243 |
| 2010/0291674 A1* | 11/2010 | Beese | C12M 23/38 435/325 |
| 2012/0138522 A1* | 6/2012 | Cirou | B01D 61/20 210/232 |
| 2012/0175012 A1* | 7/2012 | Goodwin | B01F 23/23124 141/11 |
| 2013/0101982 A1 | 4/2013 | Goodwin et al. | |
| 2014/0103077 A1* | 4/2014 | Zumbrum | C12M 23/40 141/234 |
| 2014/0349385 A1 | 11/2014 | Erdenberger et al. | |
| 2015/0029815 A1* | 1/2015 | Gebauer | C12M 23/48 366/144 |
| 2015/0117142 A1 | 4/2015 | Staheli et al. | |
| 2016/0304824 A1* | 10/2016 | Mahajan | B01F 33/4535 |
| 2017/0175066 A1* | 6/2017 | Olsen | A61J 1/12 |
| 2017/0342887 A1* | 11/2017 | McMakin | E06B 5/14 |
| 2018/0163164 A1* | 6/2018 | Husemann | C12M 41/18 |
| 2018/0187140 A1* | 7/2018 | Husemann | C12M 23/26 |
| 2018/0223233 A1* | 8/2018 | Nanba | C12M 23/48 |
| 2018/0251715 A1* | 9/2018 | Paul | C12M 23/14 |
| 2019/0015799 A1* | 1/2019 | Gebauer | B01F 33/00 |
| 2019/0367856 A1* | 12/2019 | Kilar | C12M 41/44 |
| 2022/0235304 A1* | 7/2022 | Becker | C12M 23/14 |

FOREIGN PATENT DOCUMENTS

| | | | | |
|---|---|---|---|---|
| WO | WO-2009132192 A2 * | 10/2009 | | B01F 3/04588 |
| WO | 2012125730 A2 | 9/2012 | | |
| WO | WO-2012125730 A2 * | 9/2012 | | B01F 13/0032 |
| WO | WO-2013187947 A1 * | 12/2013 | | B01F 11/0008 |
| WO | 2017118643 A1 | 7/2017 | | |

* cited by examiner a)

b)

e)

f)

g)

h)

a)

b)

HOUSING FOR HOLDING A FLEXIBLE BIOPROCESS BAG

CROSS REFERENCE TO RELATED APPLICATIONS

This application is a National Stage of International Application No. PCT/EP2017/084621 filed on Dec. 27, 2017, which claims priority to Indian Patent Application No. 201611044877 filed on Dec. 29, 2016, Indian Patent Application No. 201611044898 filed on Dec. 29, 2016 and Indian Patent Application No. 201741011286 filed on Mar. 30, 2017, all of which are incorporated herein in their entireties.

FIELD OF THE INVENTION

The subject matter disclosed herein relates to housings for holding a flexible bioprocess bag, to flexible bioprocess bags and to methods for loading a flexible bioprocess bag into a support housing. The flexible bioprocess bag can be a flexible bioprocess bag used for holding ingredients, such as a bioreactor bag.

BACKGROUND OF THE INVENTION

Single-use or disposable systems are rapidly increasing in different industries and especially in industries that require use of clean processing equipment and clean rooms, such as in the biopharmaceutical industry. Disposable systems are flexible and cost-effective and cleaning processes may be reduced or eliminated. Traditional systems comprise re-usable wetted parts in fluid contact which are typically built as stainless steel installations (tubes and vessels), which need to be cleaned or sterilized in between processes or batches. Sterilization is typically done by steam sterilization, which requires technical infrastructure and is a complex and time-consuming process. In contrast, disposable components in disposable systems provide surfaces in fluid contact that are preferably pre-sterilized and pre-qualified to all regulatory requirements. Disposable or single-use systems are replaced in between processes to eliminate cleaning and sterilization issues. Due to lower complexity in systems and auxiliary systems, disposable systems are therefore easy to adapt to different production purposes and facilities. Further, it is easy and less costly to change a product line compared to traditional equipment. Disposable systems may provide also improved reliability as well as product and operator safety in biopharmaceutical processing.

There are several kinds of disposable systems, such as mixing systems, in which disposable containers or bags are used. These containers or bags comprise often sheets of flexible material, such as plastic, plastic laminates or corresponding materials. A flexible bioprocess bag refers to a bag or pouch made of walls of similar structure preferably assembled by welding. These walls may be made of a mono or multilayer film including or not a barrier layer based on a barrier polymer like ethylene vinyl alcohol polymer (EVOH). Generally, these films may have an inner layer (in contact with the contents of the bag when filled) based on a polyolefin, preferably an ultra-low density polyethylene, pref. medical grade (ULDPE). The bag may be of cylindrical shape. Although cylindrical flexible bioprocess bags are difficult to manufacture, the cylindrical shape can be approximated and achieved by welding of multiple film panels of suitable size and shape. However, the flexible bioprocess bags can equally have cubic or parallel piped shape. Various processing and pre-conditioning steps need to be performed within these bags such as for example pre-sterilization.

One type of mixing system in which such containers or bags can be used is a bioreactor system in which cells or microorganisms can grow. Here, the bags are provided as closed and pre-sterilized components in order to avoid any contamination or inhibition in the growth of the microorganisms or cells intended for cultivation in the bioreactor.

Mixing systems include also systems used to prepare for example buffer and media, which may involve the dissolving of salts, the homogenization of suspended solids or similar.

Mixing systems include also systems for performing reactions, treatments (e.g. virus inactivation), and separations (2-phase system formation, extraction, flocculation), among other fluid processing and fluid treatment operations.

Mixing systems may comprise a support or vessel which supports or houses a disposable bag or container of the above-mentioned type. The support may be a support plate or tray for a bioreactor bag of a kind used in GE Healthcare WAVE Bioreactor®. The WAVE bioreactor is an example of a mixing system without an active mixing element, such as an agitator or impeller, submerged in the fluid. With the WAVE system, mixing is obtained by rocking the container and the platform holding the container. The vessel may also be a tank-type support which has a substantially cylindrical form, for example substantially circular cylindrical and is made of rigid material such as stainless steel to provide sufficient support for the flexible bioprocess bag or container, for example of a kind used in Xcellerex XDR™ Single-use bioreactors. The Xcellerex bioreactor is an example of a mixing system comprising an active mixing element, here a rotating impeller. The flexible container or bag is placed inside the vessel in an accurate manner so that for example different pipelines or tubes, mixers and sensors can be connected to the bag properly and accurately. WO 2005/118771 A2 discloses a disposable system of this kind.

In general, mixing systems and mixing containers or bags may be designed as a stand-alone system; or, may be part of a bioreactor, a fluid storage vessel, fluid mixing unit and so on.

Containers may vary in size from about 0.1-2000 litres. Especially at larger sizes (>20 litres), the use of vessels or rigid support structures is preferred and required for reinforcing the containers or to enable the connection of different pipelines or sensors to the containers.

The disposable containers or bags often comprise portions of rigid or semi-rigid materials for connection of tubing, ports, attachment points or general reinforcement. These rigid or semi-rigid portions provide a platform for safe and secure attachment of for example sensors, pipelines for fluids (both gas and liquid) and mixers. Further, the rigid or semi-rigid parts can reinforce and stabilize the containers and therefore facilitate placing of the containers into mixing vessels in accurate manner.

Bioprocess or mixing bags are typically provided in a housing of the bioreactor. There are numerous ways to load a flexible bioprocess bag in the housing. A standard solution for loading the flexible bioprocess bag into the rigid housing is to utilize an opening in the bioreactor wall to insert the collapsed bag through this opening (XDR Bioreactor™, GE Healthcare™. A reinforcement plate is then used to support the bag across the surface of the opening during processing and when filled with liquid. This loading method is applicable to bags that can be collapsed to a small size. Another method of loading a flexible bioprocess bag is to utilize one or multiple door segments in the rigid housing of the bioreactor. By closing the door(s) after bag loading, the rigid housing does support the bag during processing and when filled with liquid. The flexible bioprocess bag may also be loaded through an opening at the top of the rigid housing. However, this method is typically only applicable for smaller bioreactors with a height of the rigid housing not exceeding approximately 50 cm.

The above described bag loading methods all have the disadvantage of the operator needing to access the internal of the bioreactor and the rigid housing to arrange the bag in its required position, for example by docking a magnetic impeller in the bag to a magnetic drive plate in the bottom of the rigid housing. This issue with poor usability and ergonomics is in proportion to the size of the reactor.

Another loading method that provides better access to the bottom of the rigid housing is described in the product Mobius® 2000 Liter Single-Use Bioreactor from Millipore™. Here a bottom loading drawer is used. The drawer is guided on rails and can be drawn out below the rigid housing. A single-use bioreactor can be provided inside the drawer which then is pushed back to a position below the rest of the rigid housing. Another example can be seen in the ABEC CSR-Bioreactor™. Here a small carriage is provided as a bottom part of the rigid housing. The carriage can be moved to a loading position outside the rigid housing. The single use bioreactor is provided on the carriage which then is moved back into the rigid housing.

A drawback with the movable bottom part of the Millipore device is that cable and/or tubing carriers have to be employed to accommodate the change in distances between cable and/or tubing connection points at the bioreactor bottom and the system, respectively. Due to the linear motion and displacement of the movable bottom, these cable carriers are not static but need to be movable and flexible, which requires additional space underneath the rigid housing and bioreactor. Also, handling the tubing and cables during the operation of the bioreactor device may be cumbersome.

Another solution for loading the bag is where a bag is placed on the bottom of a rigid housing. A hoist connected to an end of the bag is used to lift and vertically orient the bag within the rigid housing. The rigid housing may have a door that can be opened to access the bottom of the rigid housing. An operator needs to climb up along the side of the rigid housing of the bioreactor using a ladder to connect the cable and/or tubes to ports of the bag. The ladder may be an integral part of the rigid housing or a separate ladder can be used. This loading method also poses usability issues and poor ergonomics for the operator. In other solutions, the operator may need to manually lift the bag to connect its end to a stand of the rigid housing. The stand facilitates the bag to be oriented vertically within the rigid housing. The operator may need to use a ladder to climb along the side of the housing for connecting the bag to the stand and also connect the tubes to bag ports and other cables. The connection or installation of exhaust air filters at the top of the bioreactor and bag is another operational step during bag installation and/or processing that requires the operator to interact with the top of the bag and reactor, and requires the operator to climb a ladder or enter a gallery at the top of the reactor vessel.

BRIEF DESCRIPTION OF THE INVENTION

The object of the invention is to provide a support housing for a flexible bioprocess bag, where the flexible bioprocess bag can be loaded in the housing in an easy way with good ergonomics for the operator. This is achieved by the housing comprising a side wall and a supporting part connected to a side wall to tiltably translate with respect to a longitudinal axis of the housing from an operating position to a bag loading position, wherein the supporting part comprises one or more retainers for holding the flexible bioprocess bag upon re-translation of the supporting part to the operating position. In some embodiments, the side wall comprises a first segment and a second segment, the first segment movable in relation to the second segment between an open and a closed position.

This is also achieved by a support housing having an upright side wall and a supporting part connected to the upright side wall to tiltably translate with respect to a longitudinal axis of the housing from an operating position to a bag loading position, wherein the supporting part comprises one or more retainers for holding the flexible bioprocess bag upon re-translation of the supporting part to the operating position. In some embodiments, the upright side wall comprises a first segment and a second segment, the first segment movable in relation to the second segment between an open and a closed position.

This is also achieved by a method of providing a flexible bioprocess bag in a bioreactor. The bioreactor comprises a housing having an upright side wall and a supporting part arranged to tiltably translate with respect to a longitudinal axis of the housing from an operating position to a bag loading position. The method comprises loading a flexible bioprocess bag on the supporting part arranged to the bag loading position; securing the flexible bioprocess bag on the supporting part using one or more retainers; and re-translating the supporting part to the operating position thereby positioning the flexible bioprocess bag within the housing.

The supporting part is tiltably translatable between a vertical orientation and a horizontal orientation. In the horizontal orientation, the flexible bioprocess bag is loaded on the supporting part in a convenient manner for an operator. The operator can place the flexible bioprocess bag on top of the supporting part and make required connections to the flexible bioprocess bag. Subsequently, the supporting part is translated or moved to the vertical orientation making the bag loading process easy. While loading of the flexible bioprocess bag and a corresponding loading position will be discussed hereafter, it is understood that the technical and ergonomic advantages of the invention with its improved loading position during bag loading equally apply during the removal of the bag. The supporting part can be retranslated from the vertical orientation to the horizontal orientation and the flexible bioprocess bag can be removed from the supporting part. The side wall of the support housing is designed with a double jacket to accommodate heat exchange features and transfer heat to or from the flexible bioprocess bag and bioreactor fluid volume to the jacketed vessel or vice versa. The heat exchange features enable the transfer of heat from support housing to the flexible bioprocess bag and the bioreactor fluid in the bag.

A method of cultivating cells in a bioreactor is disclosed. The bioreactor includes a support housing comprising a side wall having a first segment and a second segment, the first segment movable in relation to the second segment between an open and a closed position; wherein at least a supporting part of the first segment is arranged to be translatable from an operating position to form a bag loading position. The method includes loading the flexible bioprocess bag on the supporting part arranged in the bag loading position; securing the flexible bioprocess bag on the supporting part using one or more retainers; re-translating the supporting part to the operating position thereby positioning the flexible bioprocess bag within the housing; feeding culture medium and cells into the flexible bioprocess bag; and cultivating the cells in the flexible bioprocess bag.

A flexible bioprocess bag for holding fluids loadable in a support housing is disclosed. The flexible bioprocess bag comprises at least one interface plate, an interface plate comprising at least one fluid connection to interior of the flexible bioprocess bag, wherein the flexible bioprocess bag in a folded configuration exposes the interface plate such that the interface plate is attachable to an interface retainer on a supporting part of the support housing, the flexible bioprocess bag extends in a dimension along the supporting part while remaining unfolded narrower than the width of the supporting part; and a mating retaining member attachable to a retainer provided at the supporting part. One advantage with the disclosed is that the bag loading process becomes more convenient because the flexible bioprocess bag can be easily placed on the supporting part in the horizontal orientation. All tube or cable connections to the flexible bioprocess bag and connection to a driving unit of the flexible bioprocess bag can be done at floor level by the operator which avoids climbing on top of the bioreactor.

A flexible bioprocess bag comprising a first mixing unit configured for agitating a content of the flexible bioprocess bag and a second mixing unit, adjacent to a sparging unit, and configured for controlling the size and distribution of bubbles emanating from the sparging unit, is further disclosed.

Further, a support housing for a flexible bioprocess bag is disclosed, comprising a first drive unit and a second drive unit for connecting and driving a first mixing unit and a second mixing unit in a flexible bioprocess bag when mounted in said support housing, wherein said first drive unit is provided on a side wall or side wall segment of said support housing and wherein said second drive unit is provided on a bottom wall or bottom wall segment of said support housing.

A more complete understanding of the present invention, as well as further features and advantages thereof, will be obtained by reference to the following detailed description and drawings.

BRIEF DESCRIPTION OF THE DRAWINGS

FIG. 1a illustrates a support housing including a side wall and a supporting part in accordance with an embodiment of the invention;

FIG. 1b illustrates a side view of the support housing illustrated in FIG. 1a;

FIG. 1c illustrates the support housing of FIG. 1a having the supporting part in an extended position;

FIG. 1d illustrates a support housing including a side wall having a first segment and the second segment in accordance with an embodiment of the invention;

FIG. 1e illustrates a support housing including a side wall having a first segment and the second segment in accordance with an embodiment of the invention;

FIG. 1f illustrates a base segment tiltably movable with respect to the first segment according to an exemplary embodiment;

FIG. 1h illustrates a support housing having a first segment comprising a first portion and a second portion according to an embodiment of the invention;

FIG. 1i illustrates a support housing having a first segment comprising a first portion, a second portion and a third portion according to an embodiment of the invention;

FIG. 1j illustrates a support housing having a first segment that is collapsible with a stand for supporting the first segment according to an exemplary embodiment;

DETAILED DESCRIPTION

Figure 1:
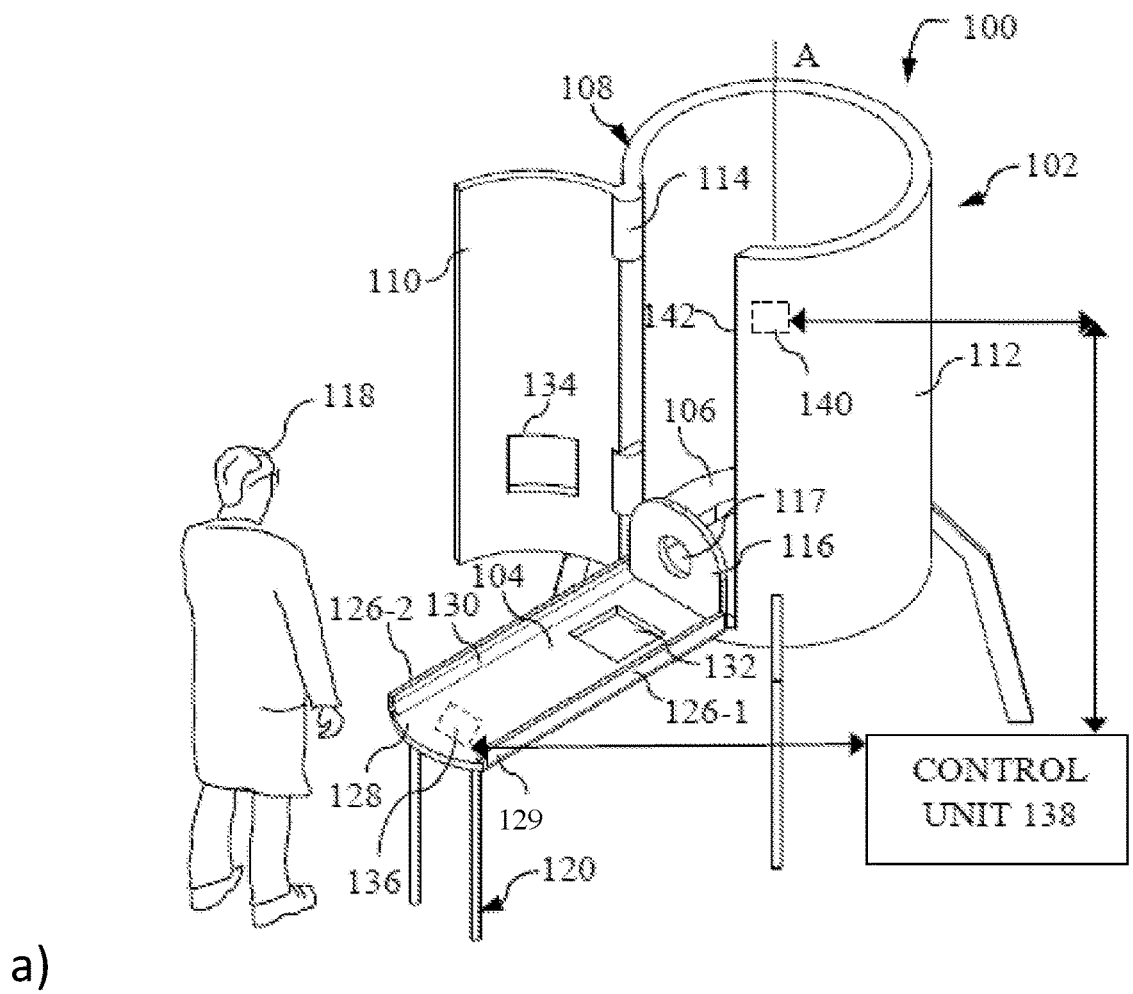
Figure 1:
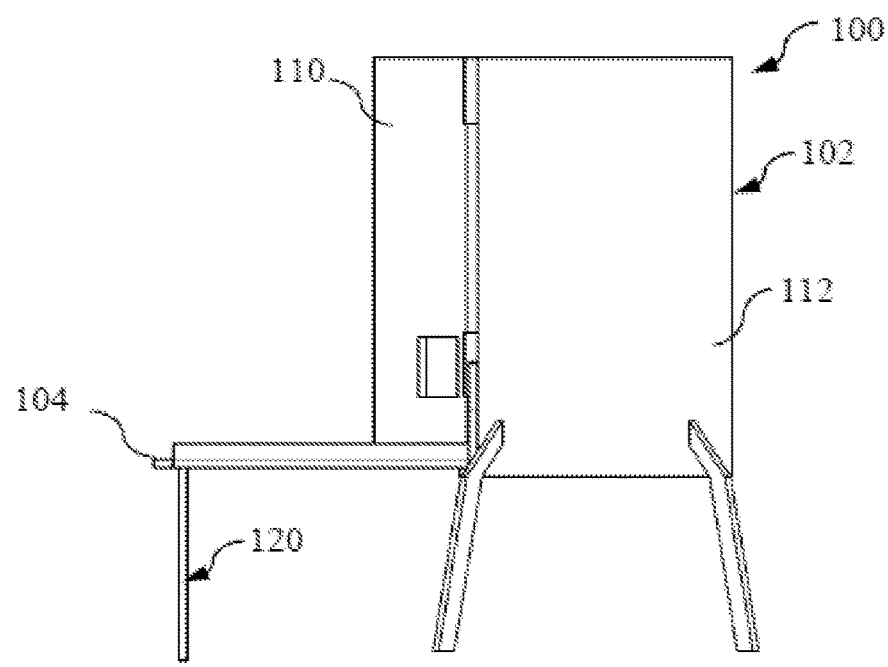
Figure 1:
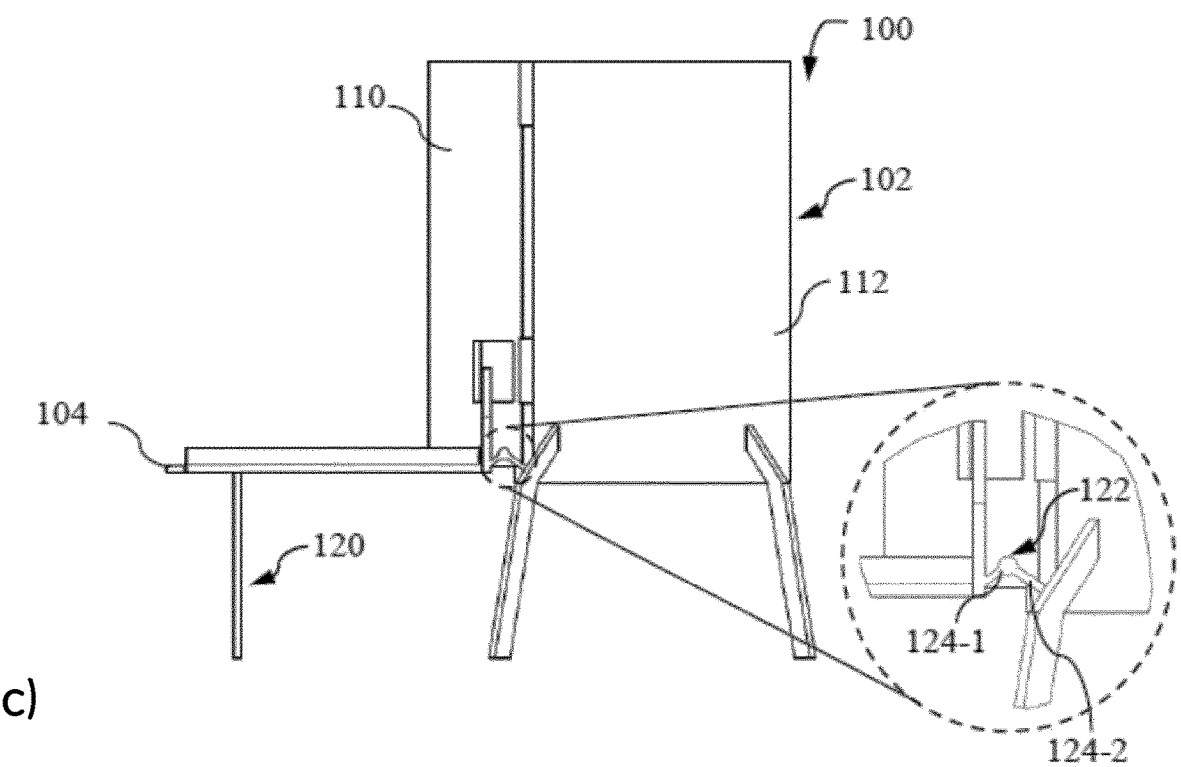
Figure 1:
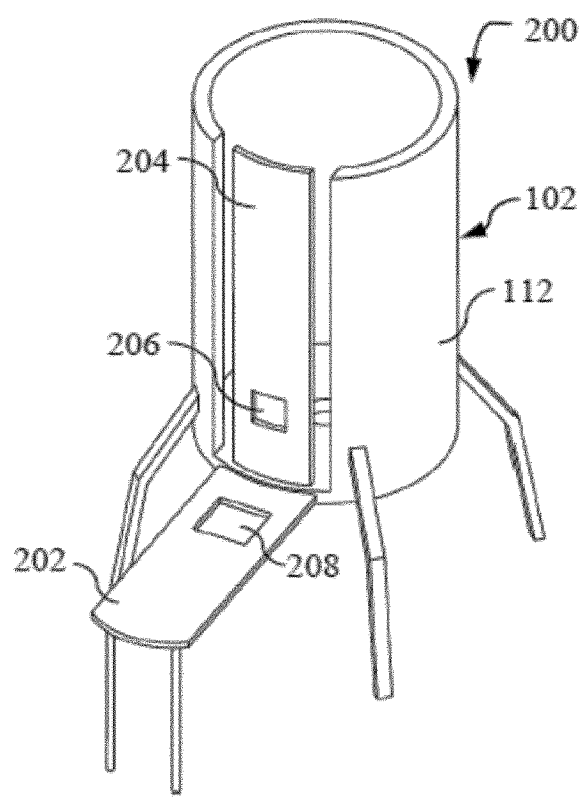
Figure 1:
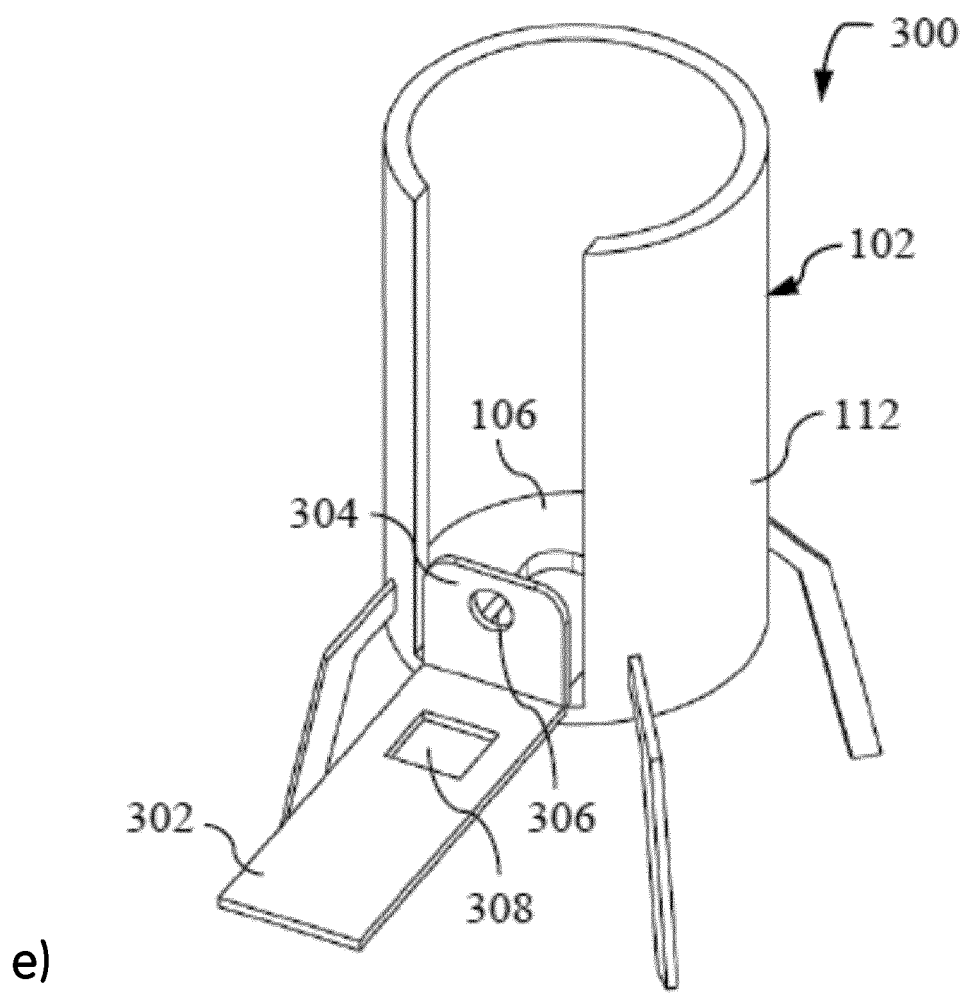
Figure 1:
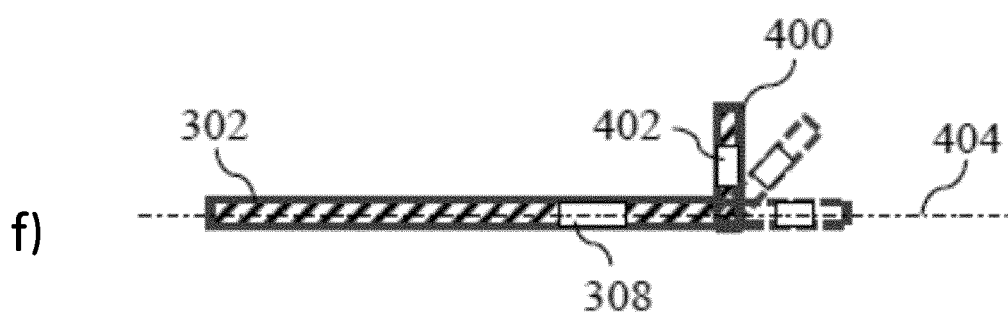

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical and other changes may be made without departing from the scope of the embodiments. The following detailed description is, therefore, not to be taken as limiting the scope of the invention.

As discussed in detail below, embodiments of a support housing for a flexible bioprocess bag, wherein the flexible bioprocess bag can be loaded in the support housing in an easy way with good ergonomics for the operator. This is achieved by the support housing comprising a side wall having a wall portion movable between an open position and a closed position. A supporting part of the support housing is arranged to be translatable from an operating position to a form a bag loading position. The supporting part may tiltably translate between a vertical orientation and a horizontal orientation. The supporting part comprises one or more retainers for holding the flexible bioprocess bag upon re-translation of the supporting part to the operating position and movement of the wall portion to the closed position.

FIGS. 1*a*-1*h* shows schematically different embodiments of a support housing in accordance with the invention. According to one embodiment of the invention, a support housing is provided, which comprises a side wall and a supporting part. The support housing (hereinafter referred to as housing) may be in a vertical orientation. The side wall includes a bottom wall and a side vertical wall defining together an internal volume in an operating position. A portion of the side wall is movable between an open and closed position. The portion of the side wall is opened and the supporting part is translatable from an operating position to a bag loading position. A flexible bioprocess bag, for example, is placed on the supporting part and is held by one or more retainers. The flexible bioprocess bag may be capable of holding ingredients that can be mixed for getting an end product, e.g. cells. However, it may be envisioned that the flexible bioprocess bag can be used to store any ingredients, such as solutions and any fluids and if necessary can be mixed to form any mixture. Upon re-translating the supporting part to the operating orientation and closing of the portion of the side wall, the flexible bioprocess bag is securely held within the housing. In another embodiment, the flexible bioprocess bag may be a standalone bag that can be used for storing ingredients (such as solutions and fluids). Alternatively, the flexible bioprocess bag can be placed in any mixing tank, mixing container and so on.

In all embodiments shown in FIGS. 1*a*-1*h*, the side wall is shown to have a cylindrical shape, however the geometrical design can be varied and still be covered by this invention. For example, a box shaped part of the housing and flexible bioprocess bag is feasible and rectangular walls may be employed for construction of the bag and housing. Other shapes and geometries of the side walls and internal volumes of the flexible bioprocess bag and the housing are feasible as well as combinations thereof, for example rectangular, triangular, hexagonal, Reuleaux triangle shaped, etc.

As shown in FIG. 1*a*, a support housing 100 (hereinafter referred to as housing 100) includes a side wall 102 and a supporting part 104 according to an embodiment of the invention. The housing 100 may be vertically oriented. The housing as shown in FIG. 1*a* may be at an elevated position from the ground. The side wall 102 comprises a bottom wall 106 and a side vertical wall 108. The side vertical wall 108 comprises a wall portion movable between an open and closed position. In an embodiment, the side vertical wall 108 comprises a first segment 110 movable in relation to a second segment 112 between an open and a closed position. The first segment 110 may extend throughout the height of the side wall 102. In another embodiment, the first segment may not extend throughout the height of the side wall 102 and may extend only to a portion of side wall 102. The first segment 110 may be movably or operably connected to the second segment 112 using different connection means 114. The connection means 114 may be for example, a hinged connection, a pivot connection, a mechanical actuator, a pneumatic actuator, an electrical actuator, a folding arm actuator and so on. In some exemplary embodiments, the first segment can be connected to the second segment using a combination of different connections means. The first segment 110 is moved to the open position and the supporting part 104 is translatable to a bag loading position. In an embodiment, the supporting part 104 is tiltably translatable from a vertical orientation to a horizontal orientation. For example, the supporting part 104 tiltably translates or moves at an angle with respect to the longitudinal axis 'A'. In the horizontal orientation, the supporting part 104 may be oriented parallel to the ground forming a table configuration. The supporting part 104 is oriented at 90° angle from the longitudinal axis 'A'. Further, a base segment 116 of the base wall 106 may be translatable to a position vertically oriented to the supporting part 104. In another embodiment, the base segment 116 may be oriented at different angles with respect to the supporting part 104. The base segment 116 includes an opening 117 for receiving an end portion of a flexible bioprocess bag that needs to be loaded in the housing 100. To load the flexible bioprocess bag in the housing 100, the flexible bioprocess bag is placed on the supporting part 104 by an operator 118. This is called a loading position of the supporting part 104. As illustrated in FIG. 1*a*, the operator 118 can stand on the ground and conveniently load the flexible bioprocess bag on the supporting part 104 which offers good ergonomics for the operator 118. In an embodiment, the supporting part 104 may have a landing gear 120 that can position the supporting part 104 in the horizontal orientation. As shown in FIG. 1*a*, in an exemplary embodiment, the landing gear 120 may include two elongated members having an end touching or resting on the ground and vertically oriented to support the supporting part 104. The landing gear 120 can be folded into the supporting part 104 when not needed. In an alternate embodiment, the landing gear 120 may be detachable from the supporting part 104. Moreover, in some embodiments, the length of the landing gear 120 can be adjusted to change the orientation and position of the supporting part 104. More specifically, the length of each member of the landing gear 120 can be elongated or shortened to adjust the orientation of the supporting part 104. The orientation can vary from a horizontal orientation to any angular orientation with respect to a horizontal plane. The landing gear 120 shown in FIG. 1a is a mere exemplary representation, and it may be envisioned that the landing gear 120 may have any other structural arrangement and can perform the same function of positioning the supporting part 104 in desired position.

In an embodiment, the supporting part 104 may be connected to the side wall 102 (either the first segment 110 or the bottom wall 106) such that the supporting part 104 is movable in relation to the side wall 102. The supporting part 104 may be movably or operably connected to the side wall 102 using different operating means. The operating means may be for example, a hinged joint, a pivot joint, a mechanical actuator, a pneumatic actuator, an electrical actuator, a folding arm actuator and so on. In some exemplary embodiments, the supporting part 104 may be connected to the side wall using a combination of different operating means. In an embodiment, the supporting part 104 may be connected to the bottom wall 106 using one or more hinge joints for example, a hinge joint 122. The hinge joint 122 is extendible as shown in FIG. 1c. In FIG. 1b the hinge joint 122 is in a folded or collapsed position. In an embodiment, there may be only one hinge joint connecting the supporting part 104 to the bottom wall 106. In another embodiment, there may be two or more hinge joints connecting the supporting part 104 to the bottom wall 106. The hinge joint 122 can be foldable and extendible as shown in FIG. 1c. The hinge joint 122 includes two arms, such as arms 124-1 and 124-2, which can move to align substantially in a straight line. When aligned in the straight line, the hinge joint 122 is extended to allow the supporting part 104 to be pulled away from the housing 100. This makes the supporting part 104 more accessible to the user. The hinge joint 122 can be folded for pushing back the supporting part 104 into position, and then can be lifted to close the housing 100. Even though the hinge joint 122 is shown to be foldable and extendible according to an embodiment, it can be envisioned that there can be other hinge means, for example, but not limited to, a telescopic hinge and an offset hinge which can perform the similar function of the hinge joint 122 and can be incorporated in the housing 100 according to various embodiments within the scope of this disclosure.

The supporting part 104 can be positioned at different angles with respect to a horizontal plane. In an embodiment the supporting part 104 is tiltably translatable to an inclination angle less than 45° from the horizontal plane to form the bag loading position. In another embodiment, the supporting part 104 may be translated to a position such that the supporting part 104 is at a height measuring less than 150 cm from the ground. The height from the ground may refer to a distance between an end portion 128 of the supporting part 104 and ground. However, in various embodiments, the supporting part 104 may be translated and positioned at different angles with respect to the ground or the horizontal plane or at different heights from the ground, by the operator 118 depending on operator's convenience. As explained earlier the operating means facilitates the supporting part 104 to be positioned at different angles or different heights. The operating means may include a functional means that enables the supporting part 104 to halt and stay at any desired angle or height without any external support when translated. The functional means may be for example, a stopper, a locking unit and so on that locks the supporting part 104 at desired position. The operator 118 can enter the housing 100 once the supporting part 104 and the first segment 110 are sufficiently opened to access the interior of the housing 100. As explained earlier, the landing gear 120 also provides additional support to the supporting part 104 for staying in the desired position. The user can step on the supporting part 104 and access the interior of the housing 100. When not in use, the landing gear 120 can be folded and positioned as part of the supporting part 104.

The supporting part 104 may have sufficient width and length to accommodate the flexible bioprocess bag. For example, the supporting part 104 may have sufficient width and a curved profile to securely hold the flexible bioprocess bag. The flexible bioprocess bag may be fastened to the supporting part 104 by one or more retainers. The retainer may be a clipping unit, a hook and loop unit, snap fit unit, a holder, a snapping belt and so on. The retainers ensure that the flexible bioprocess bag is securely positioned in place. However, in various embodiments different types of retainers may be used for holding the flexible bioprocess bag on the supporting part 104.

In an embodiment, the supporting part 104 may include flap members along its sides such a flap member 126-1 and a flap member 126-2 (i.e. retainers). The flap member 126-1 may extend along a side 129 of the supporting part 104 and the flap member 126-2 may extend along a side 130 of the supporting part 104. In an embodiment, the flap members 126-1 and 126-2 may extend along only a portion of respective sides 129 and 130. Once the flexible bioprocess bag is placed on the supporting part 104 and laid down properly, the flap members 126-1 and 126-2 can be folded to securely position or confine the flexible bioprocess bag on the supporting part 104. The supporting part 104 can be lifted to close the housing 100. The flap members 126-1 and 126-2 prevent pinching or tearing of the flexible bioprocess bag by the edges of the second segment 112 when the supporting part 104 is moved to closing position. Once the flexible bioprocess bag is inflated, the flap members 126-1 and 126-2 can be aligned such that it is properly positioned within the housing 100. More specifically, the flap members 126-1 and 126-2 may open-up when the flexible bioprocess bag is inflated. In an embodiment, the flap members 126-1 and 126-2 may be made of a material that makes it flexible for opening-up and folding. Moreover, it may be envisioned that in other embodiments, the supporting part 104 may have any other arrangements such as, a Velcro tape, snap fit members, securing belts and so on for securing the flexible bioprocess bag on the supporting part 104.

The operator 118 standing on the ground can make the connections to the flexible bioprocess bag placed on the supporting part 104 (oriented in the table configuration). This makes the bag loading process convenient for the operator 118 resulting in better user experience. Making the connections include but is not limited to, connecting tubes and valves to different ports of the flexible bioprocess bag. The ports of the flexible bioprocess bag may be one or more input ports and one or more exhaust ports which are explained in detail with respect to FIGS. 4, 6 and 7. The ports may include for example, one or more liquid ports, one or more gas ports and one or more exhaust ports. The exhaust ports may be provided at a top end portion of the flexible bioprocess bag, and one or more gas ports and the liquid ports may be provided at a bottom end portion of the flexible bioprocess bag. In another embodiment, the liquid ports, gas ports and exhaust ports may be provided at the bottom end portion or bottom of the flexible bioprocess bag. However, it may be envisioned that the liquid ports, exhaust ports and gas ports may be provided at any portion of the flexible bioprocess bag in various embodiments to make it convenient for loading the flexible bioprocess bag within the scope of this disclosure. Further, placing the flexible bioprocess bag on the supporting part 104 is discussed later in the subsequent figures. In an embodiment, the supporting part may have a tube management structure for example, but not limited to channels or trenches, for holding the tubes and connectors in order to prevent entangling of these tubes or connectors. The supporting part 104 can be translated to the vertical orientation in the housing 100, once the bag loading process is completed. This is called an operating position of the supporting part 104. In the operating position, the flexible bioprocess bag is positioned within the housing 100 and oriented in a vertical manner. The supporting part 104 and the first segment 110 are provided with an interface retainer 132 and an opening 134 respectively, that enable access to input and output ports of the flexible bioprocess bag and facilitate connecting tubes to some of these ports. The input and output ports and process of loading the flexible bioprocess bag on the supporting part of the housing are explained in detail in later figures.

In an embodiment, the housing 100 may include sensor(s) for monitoring different operations such as, opening and closing of the housing 100 and movement of the supporting part 104. The sensor(s) may be arranged in the side wall 102. The sensor(s) may be for example, but are not limited to, proximity sensors, proximity sensors with feedback mechanism, an electric circuit closure sensor, position sensor and force sensors. To detect if the supporting part 104 is in a vertical orientation or horizontal orientation or any angular orientation, a sensor 136 may be used according to an embodiment. The sensor 136 may be arranged in the supporting part 104 to determine its angular position. When the supporting part 104 is in the vertical orientation, the sensor 136 may inform a control unit 138 that it is in the vertical orientation. Consequently, the housing 100 can be closed using the first segment 110. The control unit 138 controls the opening and closing of the first segment 110. In another embodiment, the first segment 110 may be manually closed by the operator 118. In this embodiment, the control unit 138 may inform the operator 118 that the supporting part 104 is in the vertical orientation.

The housing 100 may also include a sensor for example, a sensor 140 for determining if the housing 100 is closed properly. The sensor 140 may be positioned in the side wall 102 at a location closer to the first segment 110 when it is in the closed position. However, it may be envisioned that one or more sensors can be arranged in any other location in the housing 100. The sensor 140 can detect if an edge of the first segment 110 reached closer to a periphery 142 of the side wall 102 to determine if the housing 100 is closed properly. In case the housing 100 is not closed, the control unit 138 can inform the operator 118. The operator 118 can manually close the housing 100. Alternatively, the control unit 138 can control movement of the first segment 110 to close the housing 100. Even though the sensors 136 and 140 are illustrated to be present in the housing 100, it can be envisioned that in certain embodiments, the functions performed by both these sensors can be performed by a single sensor or multiple different sensors arranged in the housing 100 within the scope of this disclosure.

In an embodiment, there may be sensor(s) capable of determining any obstacles in the path of movement of the supporting part 104 and the first segment 110. For example, sensors 136 and 140 can act as proximity sensors to determine the presence of objects near to the supporting part 104 and the first segment 110. When an object is detected in the path of movement of the supporting part 104 or the first segment 110, respective sensors 136 and 140 communicate with the control unit 138 to halt their movement. In another embodiment, the control unit 138 may inform the presence of obstacle, and the operator 118 can manually stop the movement of the supporting part 104 or the first segment 110. Other than a proximity sensor, others sensors used may be for example, but not limited to, a collision detection sensor. There may be a single sensor or multiple sensors arranged in the housing 100 to determine any obstacles or detect any collision. It may be noted that the embodiments of the housing described in FIGS. 1*d*-1*j* may have similar sensors even though it is not explicitly described or illustrated in these figures. The control unit 138 and the sensors such as, sensors 136 and 140 can together form a control system.

In an embodiment, the housing 100 may include sensor(s) positioned in different locations to identify the position of the retainers used for securing the flexible bioprocess bag. For example, the sensors are arranged in the supporting part 104 such that it can determine whether the flap members 126-1 and 126-2 are in a folded condition or open condition. In another example, the retainers may be snap fit members wound around the flexible bioprocess bag placed on the supporting part 104. The sensors can determine if the snap fit members are positioned around the flexible bioprocess bag. Here the sensors used may be proximity sensors and may be arranged in the snap fit members. If the sensors determine that the snap fit members are not proximal to the flexible bioprocess bag, then it indicates that the snap fit members are not wound around the flexible bioprocess bag. The sensors may communicate with the control unit 138 and inform the operator that the retainers are not properly positioned to secure the flexible bioprocess bag. In other embodiments, the different sensors such as, optical sensor, radio frequency sensor and RFID sensor may be used to determine if the retainers are properly securing the flexible bioprocess bag on the supporting part 104 within the scope of this disclosure.

There may be other sensors that may be capable of monitoring the different steps involved in bag loading the housing 100. The steps include orienting the supporting part 104 in the horizontal orientation, securing the flexible on the supporting part 104, orienting the supporting part 104 in the vertical orientation and closing the housing 100. The orientation of the supporting part 104 and the first segment 110 may be determined by the sensor 136 and the sensor 140 respectively. These sensors communicate with the control unit 138 to monitor and control the different steps in bag loading.

In the embodiments described in relation to FIGS. 1*d*-1*j*, some parts are identical to the parts of the embodiment described in FIG. 1*a*-*c* and those parts will have the same reference numbers and will not be described in detail again.

FIG. 1*d* illustrates a support housing 200 (hereinafter referred to as housing 200) including a side wall 102 having a first segment 202 and the second segment 112 according to an embodiment of the invention. The first segment 202 is tiltably movable in relation to the second segment 112 according to an embodiment. The first segment 202 may be operably connected to the second segment 112 using a connection means in an embodiment. The connection means in both these embodiments may be for example, a hinged unit, a pivot unit, a mechanical actuator, a pneumatic actuator, an electrical actuator, a folding arm actuator and so on. In some exemplary embodiments, the first segment 202 may be connected to the second segment 112 using a combination of different connection means. The first segment 202 is tiltably movable to an open position. In an embodiment the first segment 202 may be tiltably movable to be substantially parallel to the ground. In another embodiment, the first segment 202 may be aligned at an angle less than 45° with respect to the horizontal plane. However, in other embodiments the first segment 202 can be tilted at different angles with respect to the horizontal plane or the ground, by the operator 118 based on requirement. After opening the first segment 202, a supporting part 204 can be tiltably moved to the horizontal orientation i.e., oriented parallel to the ground. The supporting part 204 may rest on the first segment 202 which acts as a support. Alternatively, the supporting part 204 may be oriented parallel to the ground as a table configuration without the support of the first segment 202. The first segment 202 may be oriented at different angles with respect to the ground. The flexible bioprocess bag can be placed on the supporting part 204 for loading in the housing 200. The supporting part 204 and the first segment 202 are provided with an interface retainer 206 and an opening 208 respectively, that enable access to input and output ports of the flexible bioprocess bag and facilitate connecting tubes to some of these ports. The input and output ports are explained in detail later figures.

Now, FIG. 1e shows schematically a support housing 300 (hereinafter referred to as housing 300) including a side wall 102 having a first segment 302 and the second segment 112 according to an embodiment of the invention. The supporting part is described in FIG. 1a-1d as a separate unit however in this embodiment the supporting part is integral to the first segment 302. In other words, the first segment 302 may have a same structure as the supporting part and performs the same function. The first segment 302 is tiltably translatable with respect to the side wall 102 so that it is positioned in a horizontal orientation parallel to the ground. In an embodiment, the first segment 302 may be operably connected to the second segment 112 using a connection means. In another embodiment, the first segment 302 may be operably connected to the bottom wall 106 using another connection means. The connection means may be for example, a hinged unit, a pivot unit, a mechanical actuator, a pneumatic actuator, an electrical actuator, folding arm actuator and so on. In some exemplary embodiments, the first segment 302 can be operably connected to the second segment 112 or the bottom wall 106 using a combination of different connection means. In an embodiment, the first segment 302 may be translated to an angle less than 45° with respect to the horizontal plane. However, in other embodiments the first segment 302 can be tilted at different angles with respect to the horizontal plane or the ground, by the operator (e.g. the operator 118) based on the operator's convenience. The connection means may include a functional means that enables the first segment 302 to halt and stay at any desired angle with respect to the ground or the horizontal plane without any external support when translated. The functional means may be a stopper, a locking unit and so on that locks the first segment 302 at desired position.

The flexible bioprocess bag is placed on the first segment 302. The first segment 302 may have flap members similar to that explained in conjunction with FIG. 1a even though not illustrated in FIG. 1e for securely positioning or confining the flexible bioprocess bag on the first segment 302. In another embodiment, there may be retainers that help in securely positioning the flexible bioprocess bag on the first segment 302. Moreover, as illustrated in FIG. 1e, the first segment 302 may have sufficient width for securely holding the flexible bioprocess bag. The first segment 302 can be retranslated to a vertical orientation so that the flexible bioprocess bag is positioned within the housing 300.

A portion of the bottom wall 106 may be also movable to a vertical orientation or towards a vertical plane. As illustrated in FIG. 1e, a base segment 304 represents the portion of the bottom wall 106. In an embodiment, the base segment 304 is connected to the first segment 302 such that the base segment 304 also moves along with the first segment 302. For example, the base segment 304 is fixed to the first segment 302. Alternatively, the base segment 304 and the first segment 302 form a single unit. Thus, when the first segment 302 is translated to a position parallel to the ground or aligned to the horizontal plane, the base segment 304 may align to a vertical plane. The first segment 302 and the base segment 304 may form an L-shaped configuration. In other words, the base segment 304 may be aligned at an angle less than or equal to 90° or greater than 90° with respect to the first segment 302. It may be envisioned that the base segment 304 may be aligned at different angles with respect to the first segment 302 according to some embodiments. The base segment 304 includes a mating retainer 306. The flexible bioprocess bag can have an end connected to the mating retainer 306. The mating retainer 306 provides assistance in positioning or retaining the flexible bioprocess bag within the housing 300. This is further explained in conjunction with FIGS. 2 and 3. The first segment 302 is operatively connected to the base segment 304 using an operating means such as the operating means 122 in the housing 100 even though it is not illustrated in FIG. 1e. The operating means may be extendable as shown in FIGS. 1a-c, to enable the first segment 302 to be pulled out from the housing 300 so that the flexible bioprocess bag can be placed on the first segment 302. The first segment 302 can be pushed back and then translated to a vertical position for closing the housing 300. Such an operating means enables the first segment 302 to move further away from the housing 300 thereby making it convenient for the user to load the flexible bioprocess bag. The first segment 302 includes an interface retainer 308 for connecting to an interface plate of the flexible bioprocess bag. Connecting the interface plate to the interface retainer 308 assists in the holding the flexible bioprocess bag on the first segment 302 (i.e. supporting part).

In an embodiment, a base segment is operably connected to a first segment. As schematically illustrated in FIG. 1f, a base segment 400 is tiltably movable with respect to the first segment 302. The base segment 400 may be operably connected to the first segment 302. The base segment 400 may also include a mating retainer 402, similar to the interface retainer 308 in the housing 300, for performing the same function. In an embodiment, the base segment 400 is operably connected to the first segment 302 using an operating means, such as but not limited to, a hinged unit, a pivot unit, a mechanical actuator, a pneumatic actuator, an electrical actuator, a folding arm actuator and so on. In some exemplary embodiments, the base segment 400 can be operably connected to the first segment 302 using a combination of different operating means. The base segment 400 may be oriented at an angle equal to 45° with respect to a horizontal axis 404. However, the base segment 400 can be positioned at different angles with respect to the first segment 302. During bag loading, the base segment 400 can be positioned at different angles for placing the flexible bioprocess bag on the first segment 302 and connecting to the base segment 400. The base segment 400 may be re-translatable to be parallel to the ground or aligned to the horizontal axis 404. During operation after loading the flexible bioprocess bag, the first segment 302 is moved to a vertical orientation. Simultaneously, the base segment 400 also moves to a horizontal orientation or aligns to the horizontal axis 404 along with the first segment 302. In another embodiment, the base segment 400 is independently movable parallel to the horizontal axis 404 by the operator.

In the housings shown in FIGS. 1a-f, the flexible bioprocess bag can be placed on the supporting part. A first end of the flexible bioprocess bag may be connected to an upper edge of the supporting part and a second end of the flexible bioprocess bag may be connected to the base segment of the housing. When the housing is closed, the flexible bioprocess bag remains connected to the upper edge and the base segment, for it to be positioned within the housing.

Figure 1G:
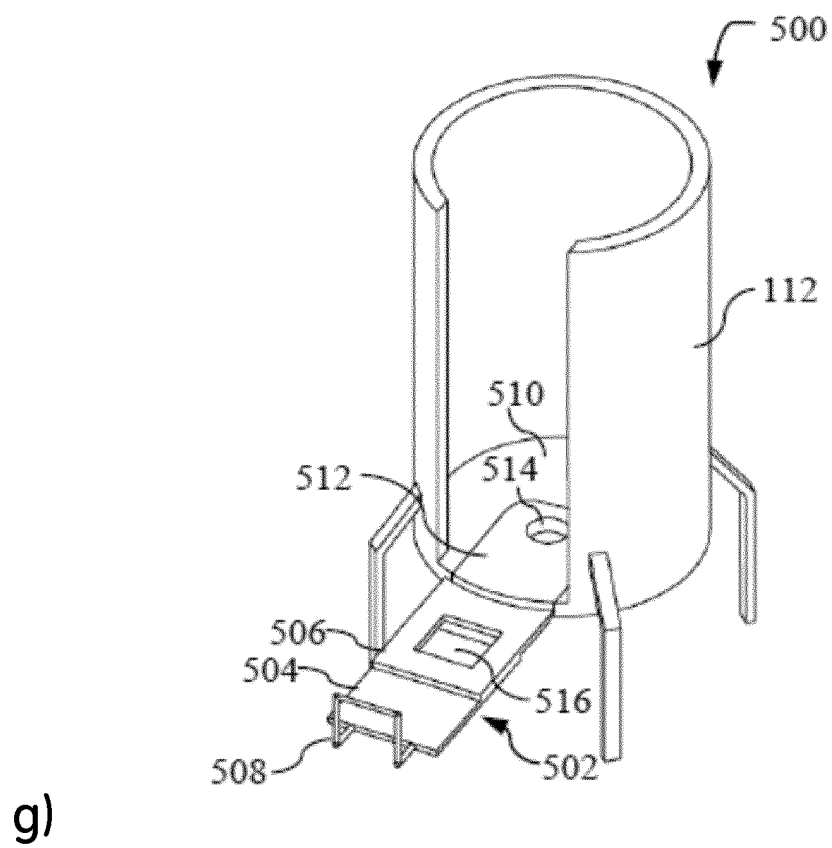
FIG. 1g illustrates a support housing having a first segment that is collapsible according to an exemplary embodiment.
Figure 1:
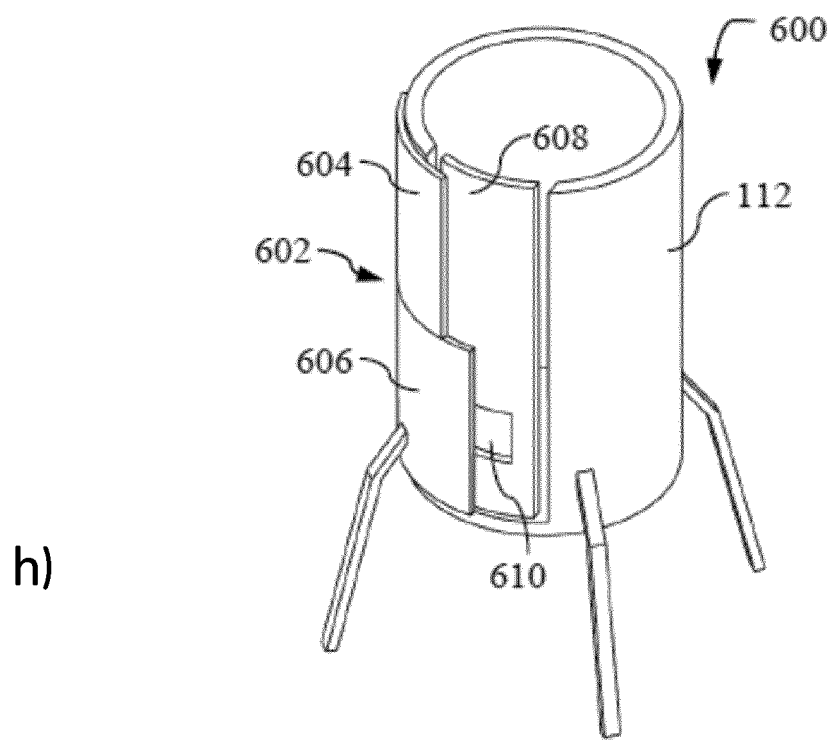
Figure 1:
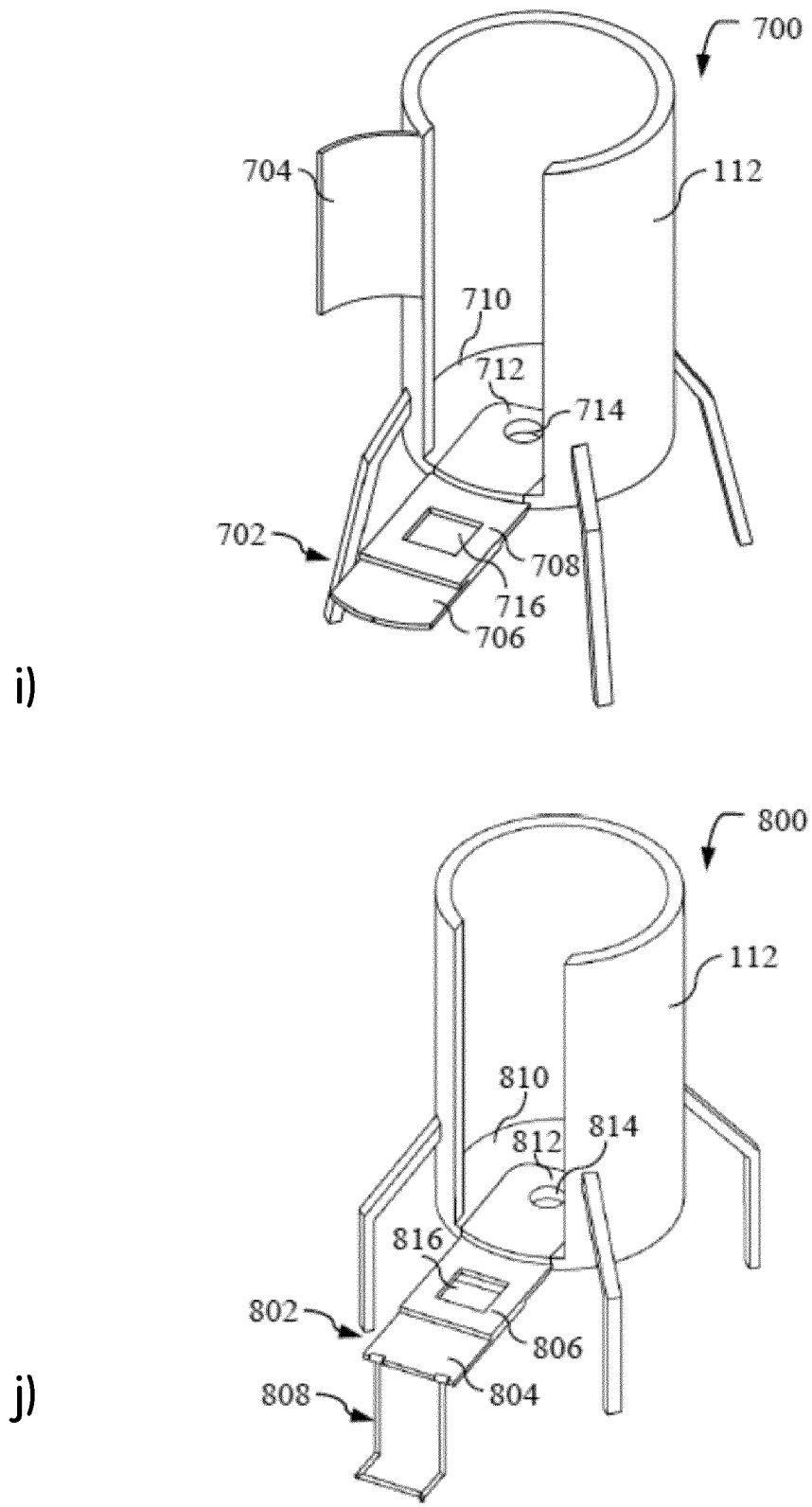

FIG. 1g schematically illustrates a support housing 500 (hereinafter referred to as housing 500) having a first segment 502 that is collapsible according to an exemplary embodiment. The first segment 502 may be collapsible and extendable in a longitudinal direction. In an embodiment, the first segment 502 is tiltably movable with respect to the second segment 112. The first segment 502 can be collapsed and then tiltably moved to position it substantially parallel to the horizontal plane. Thereafter, the first segment 502 can be extended to form a bag loading support surface. In an exemplary embodiment as illustrated in FIG. 1g, the first segment 502 may have a first portion 504 and a second portion 506. The first portion 504 may slide with respect to the second portion 506 to collapse the first segment 502. The first portion 504 may have a sliding unit and the second portion 506 may have a sliding rail (not shown in FIG. 1g only for ease of representation) in an exemplary embodiment. The sliding unit may run through the sliding rail enabling the first portion 504 to slide over the second portion 506. In other embodiments, there can be any other arrangements that facilitate the sliding movement or collapsing movement of the first portion 504 over the second portion 506. In an embodiment a retainer 508 may be used to move the first portion 504 slidably over the second portion 506. The collapsed first segment 502 can be tiltably moved to be arranged parallel to the horizontal plane. Thereafter, the first portion 504 can be slid again over the second portion 506 to extend the first segment 502 to attain a bag loading position. Here, the first segment 502 acts as the supporting part for holding the flexible bioprocess bag on it. Even though, the first segment 502 is discussed to have two portions which can collapse, it may be envisioned that the first segment 502 can have more than two portions which can collapse in different ways and then extend to form a table like configuration enabling the operator to load the flexible bioprocess bag standing on the ground in various exemplary embodiments. The housing 500 includes a bottom wall 510 having a portion i.e., a base segment 512 which is operably coupled to the first segment 502. The base segment 512 may be operably connected to the second portion 506. The base segment 512 includes a mating retainer 514. The second portion 506 of the first segment 502 includes an interface retainer 516.

FIG. 1h schematically illustrates a support housing 600 (hereinafter referred to as housing 600) having a first segment 602 comprising a first portion 604 and a second portion 606, according to an embodiment of the invention. The first portion 604 and the second portion 606 may slide over the second segment 112 to open the housing 600 as illustrated in FIG. 1h. The first portion 604 and the second portion 606 may slide separately in a transverse direction. The second segment 112 may have one or more sliding rails and the first portion 604 and the second portion 606 may have respective sliding units that slide over corresponding sliding rails to facilitate the sliding movement. Further, in an embodiment, sliding rails and sliding units may be provided along a periphery of the first portion 604 and the second portion 606 to enable movement between these two portions. However, it may be envisioned that the first portion 604 and the second portion 606 can be arranged in different configurations and opened in multiple different ways according to various exemplary embodiments of the invention. Once the housing 600 is opened, a supporting part 608 may be tiltably moved to form a table configuration. In the table configuration as described earlier, the supporting part 608 is positioned parallel to the ground or aligned to a horizontal plane. The supporting part 104 may include a holding means 610.

FIG. 1i schematically illustrates a support housing 700 (hereinafter referred to as housing 700) having a first segment 702 comprising a first portion 704, a second portion 706 and a third portion 708 according to an embodiment of the invention. As illustrated, the first portion 704 is movable between an open and closed position in a transverse direction. The first portion 704 may be operably connected to the second segment 112 using a connection means such as for example, a hinged connection, a pivot connection, a mechanical actuator, a pneumatic actuator, an electrical actuator, folding arm actuator and so on. The connection means is not illustrated in FIG. 1i only for sake convenience of representation. In some exemplary embodiments, the first segment can be connected to the second segment using a combination of different connections means. The second portion 706 may slide over the third portion 708 to open the housing 700. The second portion 706 and the third portion 708 may slide separately. The third portion 708 may have a sliding rail on it and the second portion 706 may have a sliding unit (not shown in FIG. 1i only for ease of representation) in an exemplary embodiment. The sliding unit may run through the sliding rail so that the second portion 706 slides over the third portion 708. In other exemplary embodiments, there can be any other arrangements that facilitate the sliding movement or collapsing movement of the second portion 706 over the third portion 708. It may be envisioned that the first portion 704, the second portion 706 and the third portion 708 can be arranged in different configurations and thereby opened in multiple different combinations in various embodiments of the invention. It may be noted that the housing shown in different embodiments from FIGS. 1a-e and FIGS. 1g-h can have a retainer similar to the housing 600 of FIG. 1f according to various embodiments, but is not illustrated in these figures. The housing 700 includes a bottom wall 710 having a portion i.e. a base segment 712 which is operably coupled to the first segment 702. The base segment 712 may be operably connected to the third portion 708. The base segment 712 includes a mating retainer 714. The third portion 708 includes an interface retainer 716 which can receive an interface plate of a flexible bioprocess bag positioned within the housing 700.

FIG. 1j illustrates a support housing 800 (hereinafter referred to as housing 800) having a first segment 802 comprising a first portion 804 and a second portion 806 according to an exemplary embodiment of the invention. The first segment 802 may be collapsible and extendable in a longitudinal direction. In an embodiment, the first segment 802 is tiltably movable with respect to the second segment 112 to position parallel to the horizontal plane. Thus, the first segment 802 forms a bag loading support surface. In an exemplary embodiment as illustrated in FIG. 1*g*, the first segment 802 may have a first portion 804 and a second portion 806. The first portion 804 may slide with respect to the second portion 806 to collapse the first segment 802. The first portion 804 may have a sliding unit and the second portion 806 may have a sliding rail (not shown in FIG. 1*g* only for ease of representation) in an exemplary embodiment. The sliding unit may run through the sliding rail enabling the first portion 804 to slide over the second portion 806. In other embodiments, there can be any other arrangements that facilitate the sliding movement or collapsing movement of the first portion 804 over the second portion 806. In an embodiment a retainer 808 may be used to move the first portion 804 slidably over the second portion 806. The collapsed first segment 802 can be tiltably moved to be arranged parallel to the horizontal plane. Thereafter, the first portion 804 can be slid again over the second portion 806 to extend the first segment 802 to a bag loading position. Even though, the first segment 802 is discussed to have two portions which can collapse and extend, it may be envisioned that the first segment 802 can have more than two portions which can collapse in different ways and then extend to form a table like configuration enabling the operator to load the flexible bioprocess bag standing on the ground in various exemplary embodiments.

The housing 800 includes a bottom wall 810 having a portion i.e. a base segment 812 which is operably coupled to the first segment 802. The base segment 812 may be operably connected to the second portion 806. The base segment 812 includes a mating retainer 814. The second portion 806 includes an interface retainer 816 which can receive an interface plate of a flexible bioprocess bag positioned within the housing 800.

Further it may be noted that the side walls of the housing illustrated in FIGS. 1*a*-1*j* may have a jacket configuration carrying liquids for transferring heat to ingredients in the flexible bioprocess bag according to an embodiment. The liquids flowing through the housing may be hot and may transfer appropriate heat to the ingredients. In an embodiment, the temperature of the liquids can be controlled so that desired heat is only transferred to the ingredients. In other embodiments, the side wall of the housing illustrated in FIGS. 1*a*-1*j* may have heating coil as an integral part of the side wall for heating the ingredients. The heating coil is controlled so that only desired amount of heat is only transferred to the ingredients in the flexible bioprocess bag.

Figure 2:
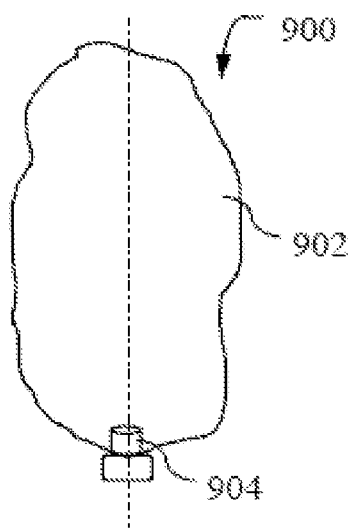
FIG. 2 illustrates a flexible bioprocess bag capable of holding fluid and other contents according to an embodiment of the invention.

Turning now to FIG. 2 illustrating a mixing system 900 capable of holding fluid and other ingredients and mixing the fluid and the ingredients according to an embodiment. The mixing system 900 includes a flexible bioprocess bag 902, which can be for example, a flexible bioprocess bag used in a single use bioreactor. The flexible bioprocess bag 902 according to the invention may be used with a mixing unit 904. The mixing unit 904 may be, for example, a fan shaped mixer, a magnetic impeller, an impeller unit and so on. The mixing unit 904 may be arranged at a bottom portion of the flexible bioprocess bag 902. In another embodiment, the mixing unit 904 may be arranged at a side bottom portion of the flexible bioprocess bag 902. However, it may be envisioned that the mixing unit 904 may be positioned at any other position at the bottom end portion of the flexible bioprocess bag 902 which would enable efficient mixing of the content according to various embodiments of the invention. Mixing of the fluids and contents is essential to enable proper interaction between the contents for further development of cell cultures. During the cell growth process, the fluids in the mixing bag (e.g. for a bioprocess application) must also be agitated in order to maintain uniform distribution of temperature, gases and nutrients. The flexible bioprocess bag 902 can be loaded into any of the housings illustrated in FIGS. 1*a*-1*i*.

The operator needs to load the flexible bioprocess bag in the housing and the content needs to be filled in the bag. There are several challenges in loading the bag, however in the disclosed housing, as the flexible bioprocess bag is loaded at ground level (i.e. the operator can place the bioprocess in the housing while standing on ground) the loading process is more convenient.

Figure 3:
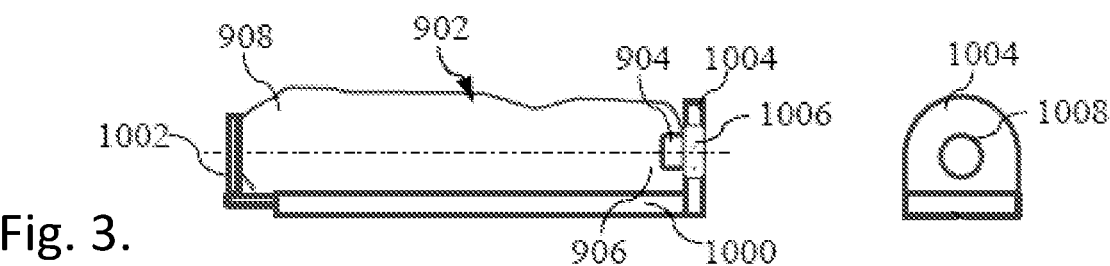
FIG. 3 illustrates a support housing having a retainer in a supporting part according to an embodiment of the invention.

Now moving to FIG. 3, the flexible bioprocess bag 902 can be placed on a supporting part 1000 in the table configuration for loading according to an exemplary embodiment. A first end portion 906 is connected to a base segment 1004 and a second end portion 908 of the flexible bioprocess bag 902 can be connected to a retainer 1002. The first end portion 906 is opposite to the second end portion 908. The flexible bioprocess bag 902 is connected to the retainer 1002 in a simple manner for illustrative purpose as shown in FIG. 3 therefore there may be different ways to connect the flexible bioprocess bag to the retainer 1002 in various exemplary embodiments. In an exemplary embodiment, the flexible bioprocess bag 902 may have a mating retaining member that can be connected to the retainer 1002. The mating retaining member may be provided in the second end portion 908 and slid into any slot provided in the retainer 1002. In another embodiment, the mating retaining member may be snap fitted to the retainer 1002. The supporting part 1000 may have retainers positioned along its sides for holding the flexible bioprocess bag 902 in place. In an embodiment, the supporting part 1000 may have flap members along the sides similar to the housing 100 of FIG. 1*a*. These flap members act as retainers to confine the flexible bioprocess bag on the supporting part 1000. The flexible bioprocess bag 902 may have the mixing unit 904 at the first end portion 906. The mixing unit 904 is operably connected to a drive unit 1006 arranged at the base segment 1004. In an embodiment, the drive unit 1006 is an integral part of the base segment 1004. In another embodiment, the drive unit 1006 may be a separate unit that can be arranged to be held by the base segment 1004. For example, the base segment 1004 may include a mating retainer 1008 for receiving the drive unit 1006. The mating retainer 1008 may be a normal slit or an opening that can hold the drive unit 1006 according to an embodiment. Alternatively, the mating retainer may be a functional or operational unit that receives and facilitates the operation of the drive unit 1006. The base segment 1004 is tiltably movable with respect the supporting part 1000. The base segment 1004 can be oriented in a vertical manner or in other words, the base segment 1004 is positioned substantially perpendicular to the supporting part 1000. While loading the flexible bioprocess bag, the mixing unit 904 is connected to the drive unit 1006 thereby connecting to the base segment 1004. The supporting part 1000 is translated to a vertical orientation positioning the flexible bioprocess bag 902 in a vertical orientation. The base segment 1004 also moves to align with the horizontal plane. The base segment 1004 and the supporting part 1000 are independently movable. In the vertical orientation, the first end portion 906 is held or supported by the base segment 1004. Further, the retainer 1002 also ensures that the flexible bioprocess bag 902 remains in the vertical orientation. During operation, liquids such as, buffer, base and other liquid contents may be fed into the flexible bioprocess bag 902 through the liquid port(s). The liquid port(s) may be connected to feed tubes which can be guided through one or more tube management structures (such as trenches) provided in the supporting part 1000 or a first segment of the housing or in the retainer 1002. The gases needed for contents in the flexible bioprocess bag 902 are fed through the gas port(s). There may be exhaust gases that gets generated and needs to be directed out through exhaust port(s). The liquid port(s), gas port(s) and the exhaust port(s) may be located at a top end portion or bottom end portion or any other portion of the flexible bioprocess bag 902 which is convenient for loading the flexible bioprocess bag according to various embodiments. These ports are not shown in FIG. 3 only for sake of convenience of representation, and hence the flexible bioprocess bag 902 may have multiple ports which are explained in detail in conjunction with FIG. 4. While loading, the tubes and other required units are connected to the exhaust port(s) and gas port(s) at ground level which makes it convenient for the user by avoiding the need for climbing to a height for accessing the top portion of the housing.

Figure 4:
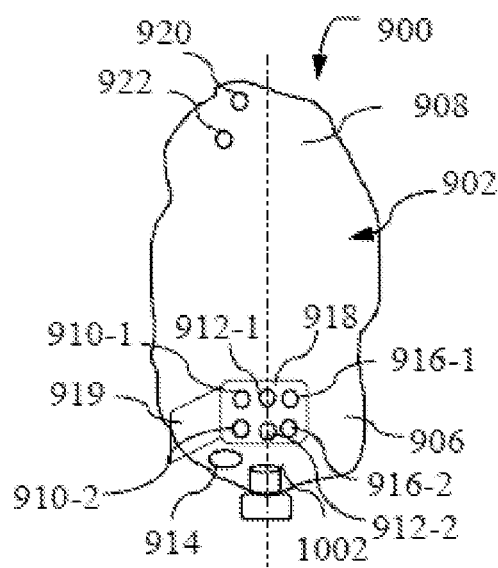
FIG. 4 illustrates a flexible bioprocess bag according to an exemplary embodiment of the invention.

FIG. 4 illustrates the mixing system 900 according to an exemplary embodiment. Hereinafter FIG. 4 is explained along with FIGS. 5a-e to describe an exemplary way of loading the flexible bioprocess bag 902 in a support housing 1100 (hereinafter referred to as housing 1100). The flexible bioprocess bag 902 includes the first end portion 906 and the second end portion 908. The flexible bioprocess bag 902 includes one or more liquid port(s) such as, a liquid port 910-1 and a liquid port 910-2, one or more gas port(s) such as, a gas port 912-1 and a gas port 912-2 at the first end portion 906. The liquid ports 910-1 and 910-2 are used for supplying liquids into the flexible bioprocess bag 902. The liquids may include for example, buffers, base, culture medium and serum which facilitate cell growth in the flexible bioprocess bag 902. The gas ports 912-1 and 912-2 are used to supply different gases such as but not limited to, oxygen, carbon dioxide and nitrogen into the flexible bioprocess bag 902. For better cell growth certain concentration of dissolved oxygen and other gases must be maintained. It may be noted that only two gas ports (such as, gas ports 912-1 and 912-2) and two liquid ports (such as, liquid ports 910-1 and 910-2) are shown to be present in the flexible bioprocess bag 902, however there can be more than two gas ports or more than two liquid ports in the flexible bioprocess bag 902 according to different exemplary embodiments. In an alternative embodiment, gas ports and/or liquid ports and respective lines are connected to the first end portion of the bag 902. In an alternate embodiment, the flexible bioprocess bag 902 may have only one liquid port and one gas port.

Another efficient way of introducing gases into the flexible bioprocess bag 902 is sparging, which involves forming bubbles in the liquids. These bubbles have large surface to volume ratio and hence dissolves more quickly than large size bubbles. A sparger 914 (also called a sparging unit) may be positioned at the first end portion 906 proximal to the gas ports 912-1 and 912-2, and liquid ports 910-1 and 910-2. In an alternate embodiment, only one sparger for example, the sparger 914 may be present for supplying gases into the flexible bioprocess bag 902 and there may not be any gas ports such as, the gas ports 912-1 and 912-2. Further, it may be also envisioned that the flexible bioprocess bag such as, the flexible bioprocess bag 902 may include more than one sparger for supplying different gases within the scope of this disclosure. These spargers may be located at different portions of the flexible bioprocess bag, so as to enable efficient mixing of the gases along with other contents for cell growth. In another embodiment, a sparger may be an integral part of the mixing unit 904. Alternatively, the sparger may be located in the receiver 1008 of the base segment 1004 (illustrated in FIG. 3) proximal to the mixing unit 904. Alternatively, the gas ports such as, the gas ports 912-1 and 912-2 may be arranged proximal to the mixing unit 904.

As different gases and liquids are added into the flexible bioprocess bag 902 there is a need to frequently measure different parameters that affect the growth of cells. The concentration of the gases and liquids can influence the cell growth rate. Hence, one or more sensors for example, a sensor 916-1 and a sensor 916-2 may be provided at the first end portion 906 of the flexible bioprocess bag 902. The sensor 916-1 and the sensor 916-2 may be used to measure different parameters. The parameters may be for example, oxygen level, nitrogen level, carbon dioxide level, buffer level, base level, cell growth level, cell death and so on. Each of these parameters may have associated parameter thresholds. Thus, the sensors 916-1 and 916-2 may determine whether parameters are within their respective thresholds. The sensors hence facilitate in frequently monitoring the cell growth in the flexible bioprocess bag and maintaining all desired parameters. Even though, only two sensors are shown to be present in the flexible bioprocess bag 902, there may be more than two sensors or only one sensor depending on the different parameters that need to be monitored according to various other embodiments within the scope of this disclosure. In an embodiment, the liquid ports (such as, the liquid port 910-1 and the liquid port 910-2), the gas ports (such as, the gas port 912-1 and 912-2) and the sensor ports (such as, the sensor port 916-1 and the sensor port 916-2) are held in an interface plate 918. The interface plate 918 may have a lid 919 which covers it and can be opened. The lid 919 may open as shown in FIG. 4 according to an embodiment; however it may be envisioned that in other embodiments, the lid may be collapsible to stay on the flexible bioprocess bag 900 or may be removed from the interface plate 918.

During cell culture process, there can be unnecessary gases (i.e. exhaust gases) than need to be expelled out from the flexible bioprocess bag 902. The flexible bioprocess bag 902 includes an exhaust port 920 that expels the exhaust gases from the flexible bioprocess bag 902. The exhaust port 920 may be positioned at the second end portion 908. The flexible bioprocess bag 902 is shown to include only one exhaust port 920 however there can be more than one exhaust port in the flexible bioprocess bag 902 according to other embodiments. The exhaust ports may be arranged at the second end portion 908 or the first end portion 906 or any other portion of the flexible bioprocess bag 902 based on convenience of expelling exhaust gases. The flexible bioprocess bag 902 can also include a gas port 922 at the first end portion 906. The gas port 922 allows gas to be fed into the flexible bioprocess bag 902. In an embodiment, the gas port 922 and the exhaust port 920 may be part of a mating retaining member. The mating retaining member can be connected to the retainer 1002. The mating retaining member may be fastened or connected to the retainer 1002 in multiple different ways according to various embodiments. In an alternate embodiment, the mating retaining member having the ports (such as one or more gas ports and one or more exhaust ports) may be connected to a top end portion of a supporting part of a housing, for example, a housing 100, 200, 300, 400, 500, 600, 700 and 800 illustrated in FIGS. 1a-j. The top end portion may have a coupling unit or a snapping unit for coupling or snapping the mating retaining member on to the supporting part. However, it may be envisioned that the top end portion may have any other connecting unit for connecting the mating retaining member to the supporting part and which can be disconnected when required by the operator to remove the flexible bioprocess bag according to various other embodiments.

Figure 5:
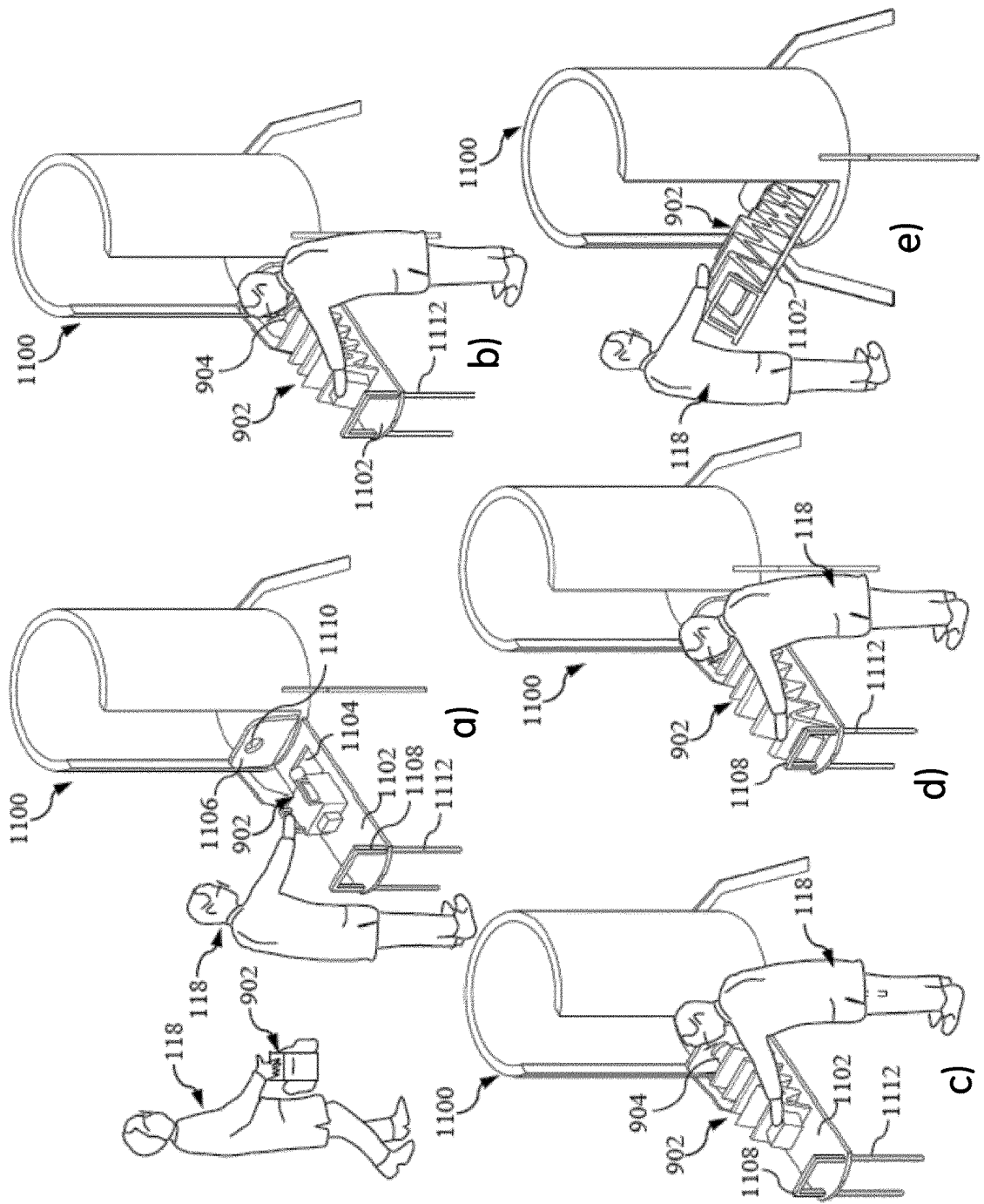
FIG. 5 illustrates an operator loading the flexible bioprocess bag on a supporting part of a support housing according to an embodiment of the invention.

Now the process of loading the flexible bioprocess bag 902 in the housing 1100 is illustrated in FIGS. 5*a*-*e*. The operator 118 may carry the flexible bioprocess bag 902 arranged in a collapsed configuration according to an embodiment. The operator 118 places the flexible bioprocess bag 902 on a supporting part 1102 as shown in FIG. 5*a*. The flexible bioprocess bag 902 may be in a collapsed configuration when placed on the supporting part 1102 according to an embodiment. Different patterns and schemes of folding or rolling the bag may be employed. In an embodiment, as shown in FIG. 5*b*-*e*, the flexible bioprocess bag 902 may be folded in a Z-shaped manner. In another embodiment the flexible bioprocess bag 902 may be arranged in a rolled or reel configuration. However, it may be envisioned that the flexible bioprocess bag can be rolled or folded in various patterns, such as but not limited to, horizontally, vertically, diagonally, any different combinations, multiple folds, repetitive folded manner and so on.

Figure 8:
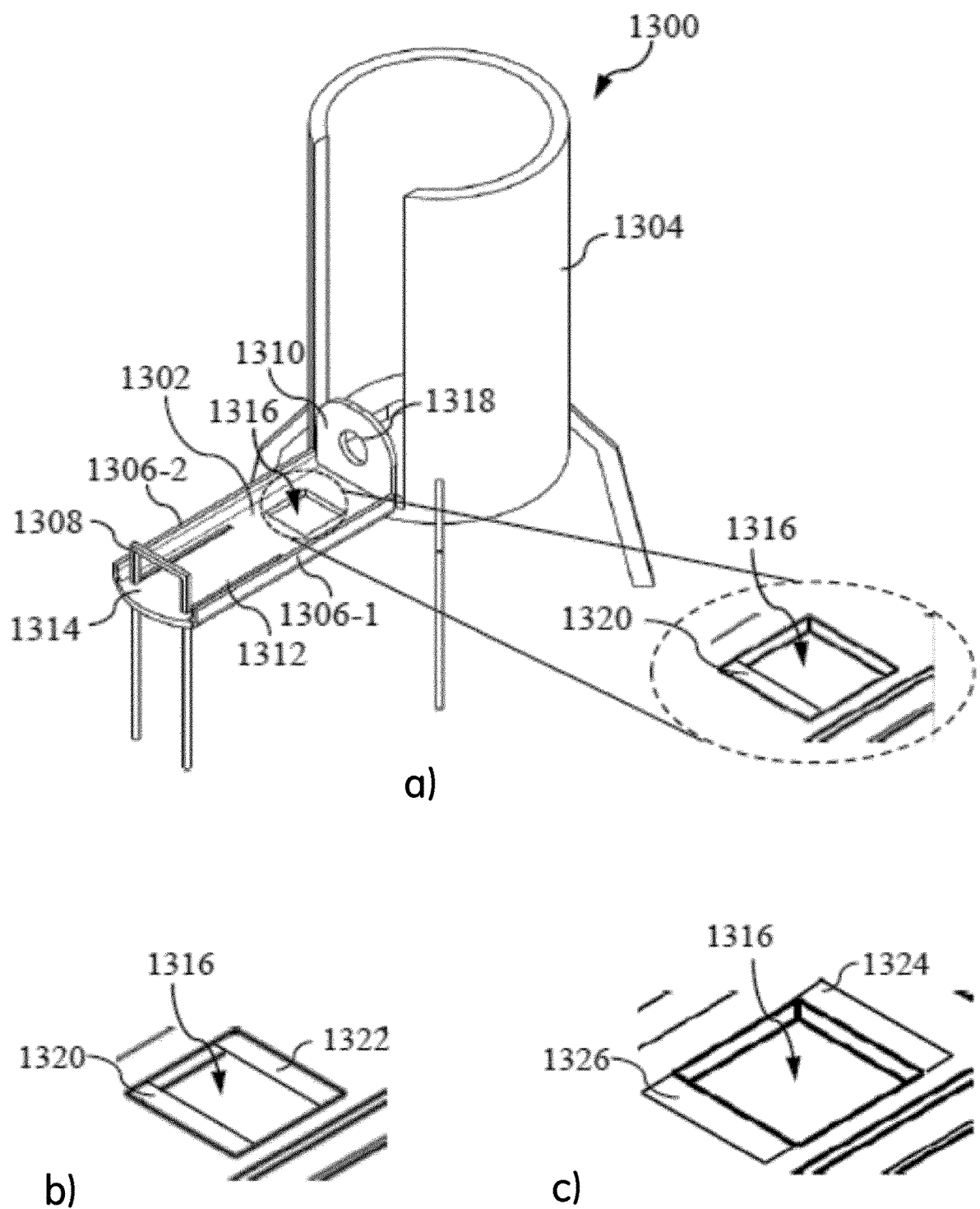
FIG. 8a illustrates a support housing for holding a flexible bioprocess bag according to an exemplary embodiment.
FIG. 8b illustrates an opening of the supporting part of the support housing according to an embodiment.
FIG. 8c illustrates an opening of the supporting part of the support housing according to an embodiment.

The collapsed configuration enables the operator to conveniently place the flexible bioprocess bag 902 on the supporting part 1102. The supporting part 1102 includes an interface retainer 1104. The operator 118 unfolds the flexible bioprocess bag 902 as shown in FIG. 5*b*. The interface plate 918 (shown in FIG. 4 is not shown in FIG. 5*a*-*e*) having multiple ports is positioned in the interface retainer 1104. In an embodiment, the interface plate 918 may be arranged or slid into a slot in the interface retainer 1104 so that it is securely positioned in place on the supporting part 1102. In another embodiment, the interface plate 918 may be snap fitted into a slot in the interface retainer 1104. Then for removing the flexible bioprocess bag, the snap fit connection can be released to disconnect the interface plate 918 from the interface retainer 1104. It may be envisioned that the interface plate 918 can be securely positioned in the interface retainer 1104 using any other coupling mechanism or connecting mechanism without deviating from the scope of this disclosure. Few exemplary embodiments of the opening (e.g. the interface retainer 1104) are described with conjunction to FIG. 8.

The mixing unit 904 is connected to a drive unit (for example the driving unit 1002) arranged in a base segment 1106 as shown in FIG. 5*c*. The driving unit is arranged in a mating retainer 1110 of the base segment 1106 (shown in FIG. 5*a*). The base segment 1106 provides additional support for positioning the flexible bioprocess bag 902 on the supporting part 1102. The second end portion 908 of the flexible bioprocess bag 902 is connected to a retainer 1108 as illustrated in FIG. 5*d*. The retainer 1108 holds the flexible bioprocess bag 902 in position on the supporting part 1102. The retainer may be designed in various configurations and the shown example is only schematic. The retainer may be designed as a single rod, plate or as a plate covering a larger or substantially the total top surface of the vessel and bag. The retainer 1108 may not be rigid, but have a hinged, (un-foldable) or telescopic design and may support multiple functions of holding and fasten other components than the bag itself. The retainer 1108 may also facilitate in unfolding the flexible bioprocess bag 902. For example, the flexible bioprocess bag 902 may be in the roll or reel configuration around a roller member. An end portion of the flexible bioprocess bag 902 may be attached to the roller member and the bag may be rolled around the roller member. The ends of the roller member may be connected to the retainer 1108 and the mixing unit 904 is connected to the mating retainer 1110. The retainer 1108 can move along the supporting part 1102 (even though not shown in FIG. 5*a*-*e* but illustrated in FIG. 8*a*), to roll the roller member so that flexible bioprocess bag 902 unfolds on the supporting part 1102. Here there is not user assistance needed for unfolding or unrolling the flexible bioprocess bag 902. Alternatively, the roller member can be rolled manually by the user to unfold the flexible bioprocess bag and then roller member can be removed. When the flexible bioprocess bag is rolled there can be reduced mechanical stress or material failure and crack as compared to being folded.

Further, the supporting part 1102 may include other retainers (not shown in FIGS. 5*a*-*e*) that may be used to fasten the flexible bioprocess bag 902 and hold it in place according to another embodiment. In another embodiment, the supporting part 1102 may have flap members along its sides for securely positioning the flexible bioprocess bag 902. The flap members are described in conjunction with FIGS. 1*a*-*c*. The mating retainer 1110 of the base segment 1106 may also receive the sparger or sparging unit 914 according to an embodiment. The mating retainer 1110 enables the sparger 914 to be in place on the supporting part 1102 and also adds to the support for the flexible bioprocess bag 902. The mating retainer 1110 may also have the drive unit which can get connected to the mixing unit 904 as explained earlier. In another embodiment, the sparger 914 may be placed in another mating retainer (not shown in FIG. 5*a*-*e*) provided in the base segment 1106. The housing 1100 can be closed by the operator 118 by moving the supporting part 1102 to a vertical position as illustrated in FIG. 5*e*. Before closing the housing 1100, a landing gear 1112 can be collapsed or folded into the supporting part 1102. In another embodiment, the landing gear 1112 can be disconnected from the supporting part 1102.

Figure 6:
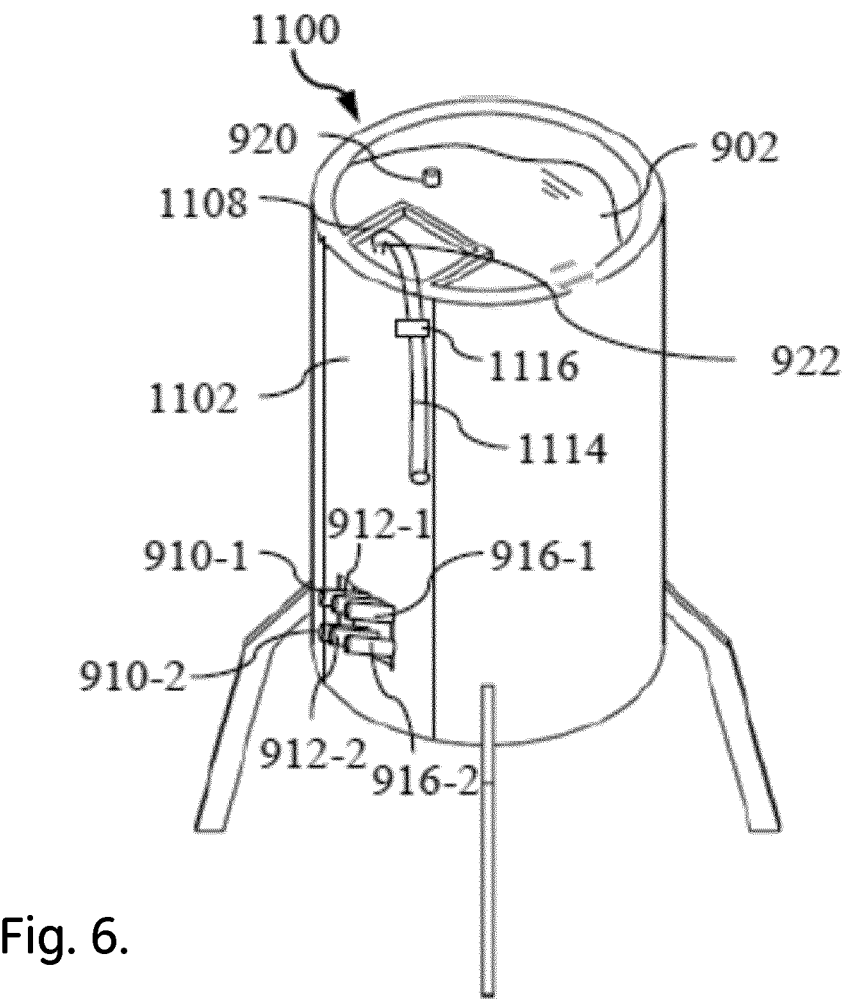
FIG. 6 illustrates the flexible bioprocess bag of FIG. 5 loaded in the support housing according to an embodiment of the invention.

While placing the flexible bioprocess bag 902, in an exemplary embodiment, the interface plate 918 may be positioned in the slot of the interface retainer 1104, such that the liquid ports 910-1 and 910-2, the gas ports 912-1 and 912-2 and the sensors 916-1 and 916-2 can project out through the holding means 1104. FIG. 6 illustrates the liquid ports 910-1 and 910-2, the gas ports 912-1 and 912-2 and the sensors 916-1 and 916-2 projecting out from the interface retainer 1104. In another embodiment, the interface retainer 1104 may be arranged at any other location on the supporting part 1102 and accordingly the liquid ports 910-1 and 910-2, the gas ports 912-1 and 912-2 and the sensors 916-1 and 916-2 may be configured in the flexible bioprocess bag 902 so as to align with the interface retainer 1104. The interface plate 918 positioned in the interface retainer 1104 also provides additional assistance in placing the flexible bioprocess bag 902 in place. The interface plate 918 may be configured to include additional ports or lesser number of ports (such as liquid ports, exhaust ports, gas ports and sensor ports) based on the requirement of the application (for example a bioprocess application) in other embodiments within the scope of this disclosure.

When the supporting part 1102 is in the table configuration, the operator 118 can connect a gas tube (i.e. a gas tube 1114) to the gas port 922. The gas tube 1114 may be connected to respective gas reservoirs for supplying gas into the flexible bioprocess bag 902. In another embodiment, when the supporting part 1102 moves to the operating position, the gas tube 1114 connects to the gas port 922 without user assistance, once the flexible bioprocess bag 902 is unfolded to retain on the supporting part 1102. The gas tube 1114 may be attached to the supporting part 1102 by a fastening member 1116 according to an embodiment. Alternatively, the flexible bioprocess bag 902 may unfold after the supporting part 1102 is moved to the operating position and subsequently the gas tube 1114 gets connected to the gas port 922 without any user assistance. In this embodiment, the gas tube 1114 may be already attached to the supporting part 1102. Another way in which a gas tube is attached to the supporting part is described in conjunction with FIG. 10. Even though only one tube is shown FIG. 6, there can be more than one tube that may be connected to different ports such as, liquid ports and gas ports according to various embodiments within the scope of the disclosure. Further, the operator 118 may also connect exhaust filter(s) to the exhaust port 920. The operator 118 is able to load the flexible bioprocess bag 902 and make connections to the liquid ports, the exhaust ports, the gas ports and the sensor ports while standing on the ground thereby providing good ergonomics and user experience. In an alternate embodiment, the exhaust port 920 and the gas port 922 (as shown in FIGS. 4 and 6) may be arranged in a single unit (as a mating retaining member) for example, a manifold, and connected to the retainer 1108. Once the flexible bioprocess bag 902 is loaded, the supporting part 1102 is translated to vertical orientation to close the housing 1100. Here, the flexible bioprocess bag 902 is placed within the housing 1100. After completion of cell culture process, the contents of the flexible bioprocess bag 902 may be removed. Thereafter, the supporting part 1102 can be translated to the table configuration (i.e. the supporting part 1102 is positioned parallel to the ground), and then tubes and other connections can be disconnected. The flexible bioprocess bag 902 can be removed from the supporting part 1102 conveniently by the operator to complete the unloading process.

Figure 7:
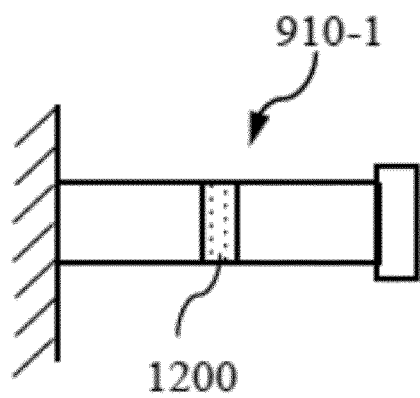
FIG. 7 illustrates a port of the flexible bioprocess bag of FIG. 5 according to an embodiment of the invention.

For ports and lines introducing fluid into the volume and internal of the bag, check valve arrangements may be applied to avoid any draining or backflow of reactor fluid into the lines. The check valves may be arranged in the line upstream the connection to the bag, at the connection of the bag or inside the bag at the outlet of the connecting line, tube or port which is known and disclosed in US2016/0194592, which is hereby incorporated by reference in its entirety. For example, if liquids are fed into the flexible bioprocess bag 902 from the bottom, there is a need to ensure that there is no back flow of the liquids. FIG. 7 illustrates the liquid port 910-1 according to an embodiment. As the liquid port 910-1 is arranged at the first end portion 906, the liquid filled in the flexible bioprocess bag 902 may flow back outward. The liquid port 910-1 includes a check valve 1200 that restricts the outward flow of liquid from the flexible bioprocess bag 902. The check valve 1200 only allows inward flow of the liquid thus prevents any loss of liquid from the flexible bioprocess bag 902. Similarly, the liquid port 910-2 may also have a check valve similar in structure and configuration of the check valve 1200. Further, it may be envisioned that the liquid port may have any other structural component that prevents the outward flow of the liquid other than a check valve according to other embodiments within the scope of this disclosure.

FIG. 8a illustrates a support housing 1300 (hereinafter referred to as housing 1300) for holding a flexible bioprocess bag according to an embodiment. The housing 1300 includes a first segment 1302 operatively connected to a second segment 1304. The first segment 1302 tiltably opens to access the interior of the housing 1300. The operator 118 can place the flexible bioprocess bag on the first segment 1302 which acts as a supporting part. The first segment 1302 includes flap members 1306-1 and 1306-2 along its sides which act as retainers. Once the flexible bioprocess bag is placed on the first segment 1302 and laid down properly, the flap members 1306-1 and 1306-2 can be folded to securely position or confine the flexible bioprocess bag on the first segment 1302. A second end portion of the flexible bioprocess bag may need to be connected to a retainer 1308. The flexible bioprocess bag may have a first end portion that needs to be connected to a base segment 1310. In order to connect, the flexible bioprocess bag needs to be unfolded to some extent by the operator 118. The retainer 1308 can be moved along a track 1312. In an embodiment, the track 1312 may be in the form of a sliding rail, and the retainer 1308 may have a sliding unit that enables it move along the track 1312. The operator 118 can connect the second end portion of the flexible bioprocess bag to the retainer 1308 and it can be moved to a position at an end portion 1314 of the first segment 1302. The track 1312 or the retainer 1308 may include a locking unit that can halt the movement of the retainer 1308 in the track 1312. The locking unit can position the retainer 1308 at any desired position in the track 1312. In an alternate embodiment, the movement of the retainer 1308 along the track 1312 can be controlled by a control unit (for example, the control unit 138 shown in FIG. 1a. Once the retainer 1308 moves, it unfolds the flexible bioprocess bag (e.g. the flexible bioprocess bag 900) along the first segment 1302. Considering the bag arrangement illustrated in FIGS. 5b-e, the retainer 1308 can unfold the flexible bioprocess bag folded in the Z-shaped manner. The flexible bioprocess bag may be unfolded when the first segment 1302 is in the table configuration or in the operating position. It may be noted that the structure of the retainer 1308 illustrated here is according to one embodiment, and the retainer 1308 can have any other structural configuration or arrangement in other embodiments within the scope of this disclosure.

The first segment 1302 includes an interface retainer 1316 for receiving an interface plate of the flexible bioprocess bag (for example, the interface plate 918 of the flexible bioprocess bag 902. The base segment 1310 includes a mating retainer 1318 for holding a drive unit which drives a mixing unit in the flexible. This is explained in detail earlier.

The interface retainer 1316 may include a shutter 1320 that can move to increase the size of the interface retainer 1316. The operator (such as the operator 118) can insert the interface plate within the interface retainer 1316 while placing the flexible bioprocess bag 902 on the first segment 1302. The second end portion of the flexible bioprocess bag 902 is connected to the base segment 1310 through the mating retainer 1318. When the first end portion of flexible bioprocess bag 902 is connected to the retainer 1308, the shutter 1320 can be moved to widen the interface retainer 1316.

In another embodiment as shown in FIG. 8b, the interface retainer 1316 can include two shutters, the shutter 1320 and the shutter 1322. The operator may insert the interface plate of the flexible bioprocess bag 902 in the interface retainer 1316. The size of the interface retainer 1316 can be varied by moving the shutters 1320 and 1322. While connecting the first end portion 906 of the flexible bioprocess bag 902 to the base segment 1310, the shutter 1322 may be in a collapsed state and the shutter 1320 may remain in the drawn-out state. When the second end portion 908 is connected to the retainer or a top end portion of the supporting part, the shutter 1320 may be moved to a collapsed state and the shutter 1322 may move to the drawn-out state. The movement of the shutters 1320 and 1322 may be controlled by the operator or it may be automatically controlled for example, by the control unit 138. Thus, the size of the interface retainer 1316 can be varied based on the requirement.

In an embodiment as illustrated in FIG. 8c, the interface retainer 1316 may be capable of moving in the first segment 1302. As illustrated there are two shutters 1324 and 1326 provided at two sides of the holding means 1316. These shutters can move between a collapsed and drawn-out sate. The operator can position the interface plate in the interface retainer 1316, and when connecting the second end portion of the flexible bioprocess bag 902 to the retainer 1308 the shutter 1326 can change from the drawn-out state to the collapsed state thereby moving the interface retainer 1316. The operator may connect the first end portion of the flexible bioprocess bag 902 to the base segment 1310 through the receiver 1318, then the shutter 1324 can change from the drawn-out state to the collapsed state thereby moving the interface retainer 1316. Here, the shutter 1326 moves from the collapsed state to the drawn-out state. As the interface retainer 1316 moves, it helps the operator in conveniently loading the flexible bioprocess bag 902 on the first segment 1302. Even though, few embodiments of the structural configuration of the interface retainer 1316 is illustrated in FIGS. 8a, 8b and 8c, it may be envisioned that the interface retainer 1316 can have different structural arrangements for conveniently receiving the interface plate to aid bag loading, within the scope of this disclosure as there are numerous embodiments and alternatives to mentioned shutter mechanism to achieve the desired positioning, fastening and release of interface plates.

Figure 9:
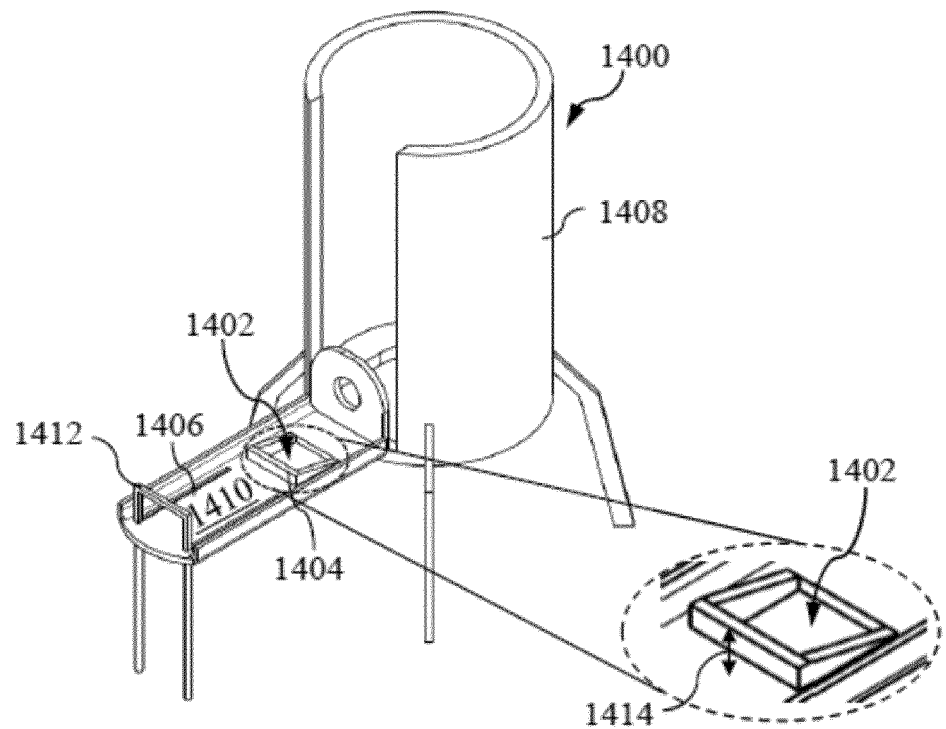
FIG. 9 illustrates a support housing having a receiver for holding a bag interface plate of the flexible bioprocess bag according to an embodiment of the invention.

FIG. 9 illustrates a support housing 1400 (hereinafter referred to as housing 1400) for holding a flexible bioprocess bag according to yet another embodiment. The housing 1400 may have a similar structure and configuration as the housing 1300 and accordingly include similar parts that perform the same function. The parts that are similar in housing 1400 and 1300 may not be described again in detail with respect to FIG. 9. The housing 1400 may have an interface retainer 1402 with a projecting structure 1404. The projecting structure 1404 may have a slot for receiving the interface plate of a flexible bioprocess bag. The flexible bioprocess bag can be placed on a first segment 1406 operably connected to a second segment 1408. The interface plate can be slid into the slot of the projecting structure 1404 in an angular direction while connecting both end portions of the flexible bioprocess bag. After the interface plate is placed in the slot, the projecting structure 1404 can be collapsed to align to an inner surface 1410 of the first segment 1406. Now while unloading the flexible bioprocess bag, the projecting structure 1404 can be drawn-out from the collapsed state for sliding the interface plate out from the slot as illustrated in the zoomed view. The movable retainer 1412 and the projecting structure 1404 assist the operator 118 to conveniently remove the flexible bioprocess bag from the first segment 1406. In another embodiment, the projecting structure 1404 can be moved to different heights in vertical direction (shown by arrow 1414) so that the interface plate can slid into the slot at varying angles. This facility provides additional assistance for the operator to load the flexible bioprocess bag 902.

Figure 10:
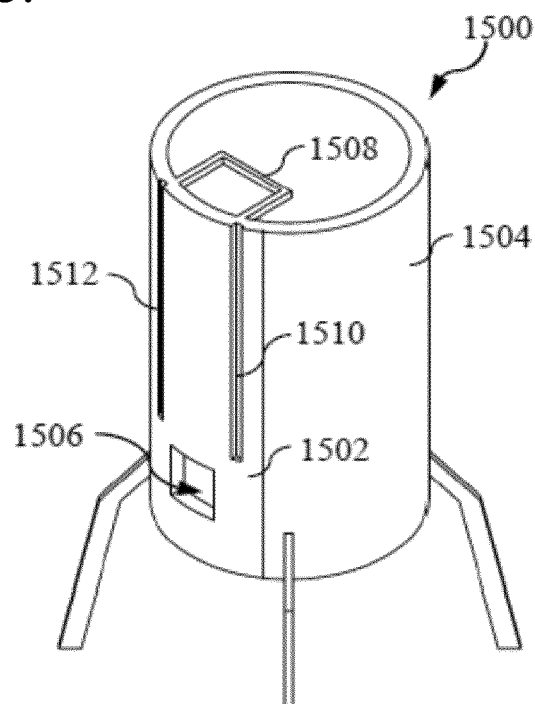
FIG. 10 illustrates a support housing having tube trenches for receiving and holding tubes connected to the support housing according to an embodiment of the invention.

Now moving on to FIG. 10 illustrating a support housing 1500 (hereinafter referred to as housing 1500) for holding a flexible bioprocess bag according to still yet another embodiment. The housing 1500 includes a first segment 1502 operatively connected to a second segment 1504. The first segment 1502 tiltably opens to access the interior of the housing 1500 even though not illustrated in FIG. 10. The first segment 1502 may include an interface retainer 1506 and a retainer 1508. The function of the opening and retainer is explained in detail in conjunction with FIGS. 1a-i and 6, hence not described here. The first segment 1502 includes two trenches for example, a trench 1510 and a trench 1512. After loading the flexible bioprocess bag in the housing 1500 and connecting tubes to the flexible bioprocess bag, the tubes can be arranged in the trenches 1510 and 1512 by the operator 118. The trenches 1510 and 1512 form part of a tube management structure that avoids entangling of tubes. In an embodiment, the trenches 1510 and 1512 may have additional members that securely fit the tubes in them. In another embodiment, there may be clipping or snapping members provided for securely positioning the tubes in place within the trenches. The tube management structure (i.e. the trenches 1510 and 1512) illustrated here is according to one of an exemplary embodiment, and hence it may be envisioned that the tube management structure may have any other structural arrangement for holding the tubes in an organized or concealed manner. Equally, the trenches may be larger in size and depth and may also protrude from the external surface of the first segment 1502 to accommodate the required number and size of tubing. The trenches may also be employed for routing cables, for example cables connecting to sensors (like a pressure sensor measuring the head pressure in the gas at the top of the bag) or cables connecting to remote controlled components such as for example valves.

Figure 11:
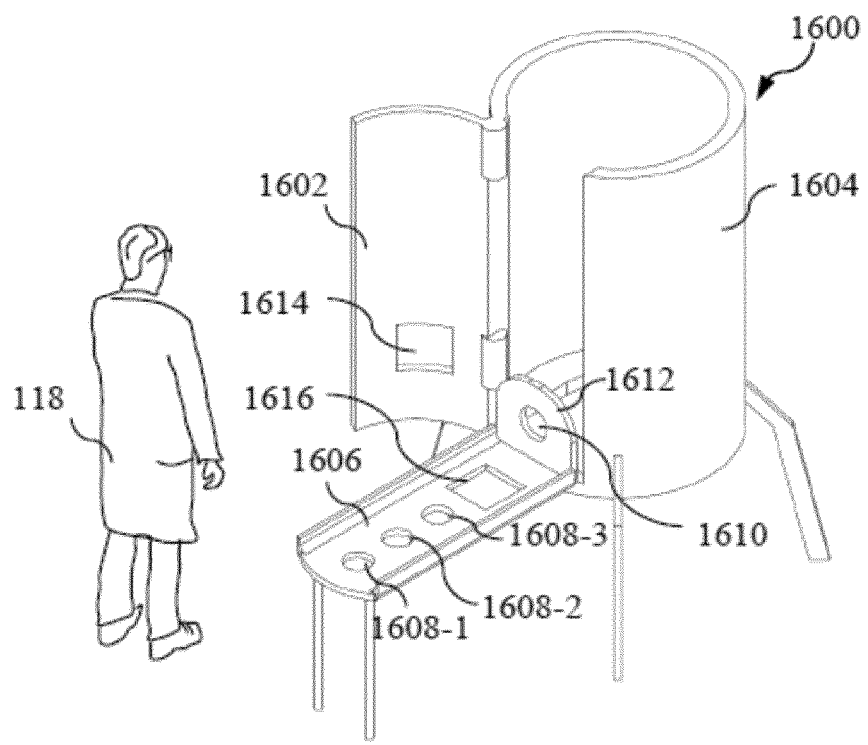
FIG. 11 illustrates a support housing having a supporting part having multiple receivers capable of receiving mixing units of the flexible bioprocess bag according to an embodiment.
Figure 12:
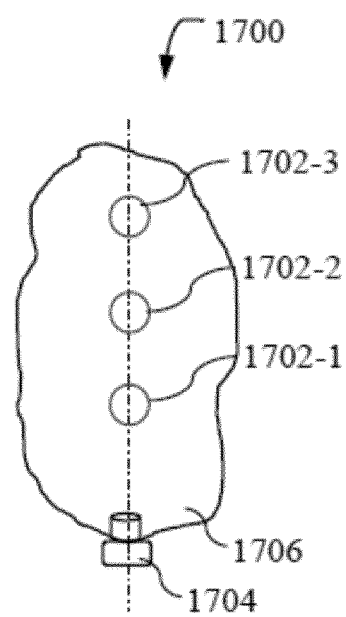
FIG. 12 illustrates a flexible bioprocess bag having multiple mixing units to be arranged on the supporting part of FIG. 11.

FIG. 11 illustrates a support housing 1600 (hereinafter referred to as housing 1600) for holding a flexible bioprocess bag according to yet another exemplary embodiment. The housing 1600 includes a first segment 1602 operatively connected to a second segment 1604. The first segment 1602 opens and closes in a transverse direction. A supporting part 1606 includes one or more openings such as, a mating retainer 1608-1, a mating retainer 1608-2 and a mating retainer 1608-3 for holding drive units. The openings may be aligned in line as illustrated in FIG. 11. Even though three drive units are held in the corresponding mating retainers, the housing 1600 may have one or more drive units. A flexible bioprocess bag 1700 as schematically illustrated in FIG. 12 is loaded in the housing 1600. A flexible bioprocess bag 1700 includes a mixing unit 1702-1, a mixing unit 1702-2 and a mixing unit 1702-3 arranged along its side portion as illustrated in FIG. 12 according to an embodiment. When the supporting part 1606 is positioned in a table configuration, the flexible bioprocess bag 1700 is placed on the supporting part 1606 such that the mixing units 1702-1, 1702-2 and 1702-3 are operatively connected to corresponding drive units arranged in the mating retainers 1608-1, 1608-2 and 1608-3. For sake of convenience of illustration, the drive units are not illustrated in FIG. 12. The supporting part 1606 is moved to a vertical orientation so that the flexible bioprocess bag 1700 is positioned in a vertical orientation within the housing 1600. As described earlier, this is an operating position of the housing 1600 and the flexible bioprocess bag 1700. In this embodiment, the mixing units are present only at the side portion of the flexible bioprocess bag 1700, however in other exemplary embodiments, the mixing units may be present in the supporting part 1606 and another mixing unit 1704 may be arranged in a bottom portion 1706 of the flexible bioprocess bag 1700 which is illustrated in FIG. 12. The mixing unit 1704 is operatively connected to a drive unit through a mating retainer 1610 in a base segment 1612 of the housing 1600. The first segment 1602 and the supporting part 1606 may have an opening 1614 and an interface retainer 1616. The function of the opening and the interface retainer are described with respect to the earlier figures and hence not described in detail here.

Figure 13:
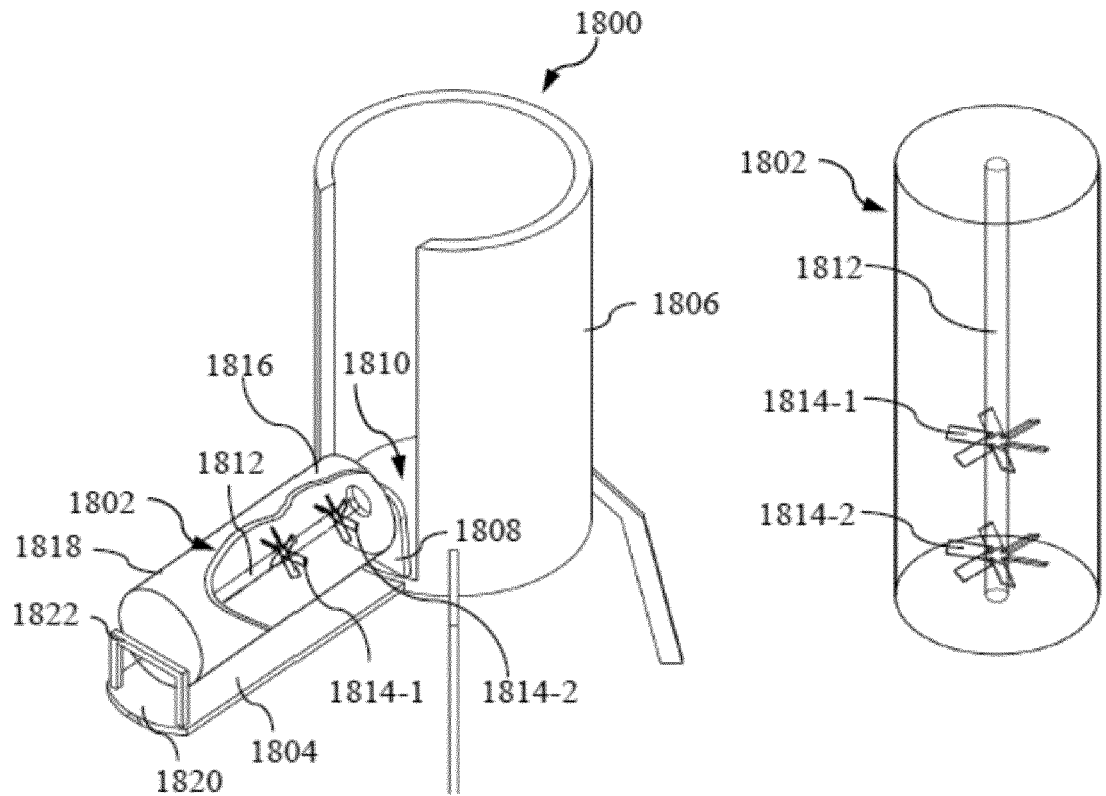
FIG. 13 illustrates an exemplary flexible bioprocess bag arranged in a support housing according to an embodiment.

FIG. 13 illustrates a support housing 1800 (hereinafter referred to as housing 1800) for holding another flexible bioprocess bag 1802 according to an exemplary embodiment. The housing 1800 includes a first segment 1804 (i.e. a supporting part) operably connected to a second segment 1806. A base segment 1808 which is a portion of a base wall 1810 of the housing 1800 also moves to the vertical orientation when the first segment 1804 is arranged in a horizontal orientation parallel to the horizontal plane or the ground. The base segment 1808 and the first segment 1804 may move together or separately to respective orientation. The flexible bioprocess bag 1802 can be placed on the first segment 1804 in the table configuration. The flexible bioprocess bag 1802 includes a mixing unit 1810 having a shaft 1812 holding a mixing blade 1814-1 and a mixing blade 1814-2. The shaft 1812 may be connected to a first end portion 1816 and a second end portion 1818 of the flexible bioprocess bag 1802. In another embodiment, the shaft 1812 may be only connected to the second end portion 1818. When the flexible bioprocess bag 1802 is positioned on the first segment 1804, the end of the shaft 1812 connected to the first end portion 1816 engages with a drive unit present in the base segment 1808.

In an embodiment, the shaft 1812 may be driven by a drive unit arranged in second end portion 1818 of the flexible bioprocess bag 1802. The drive unit may be arranged in the flexible bioprocess bag 1802. Alternatively, the drive unit may be positioned at an end portion 1820 of the first segment 1804. When the second end portion 1818 is connected to a retainer 1822, the shaft 1812 is coupled to the drive unit. The end of shaft 1812 may be automatically or manually coupled to the drive unit. In yet another embodiment, the drive unit may be mounted on the second segment 1806 which is fixed. When the first segment 1804 is moved to close the housing 1800 after bag loading, the end of the shaft 1812 automatically couples with the drive unit.

In an embodiment, the flexible bioprocess bag 1802 may include two shafts and a shaft may be connected to the mixing blade 1814-1 and another shaft to the mixing blade 1814-2. In this case the shafts may be driven by two separate drive units for running the mixing blades such as, the mixing blades 1814-1 and 1814-2. In some embodiments, shafts and/or impellers may be collapsible or foldable to allow a compact size during transport and storage of the bag and may be brought into the respective shape and size for operation during the bag installation procedure, bag inflation, bag filling or processing.

Figure 14:
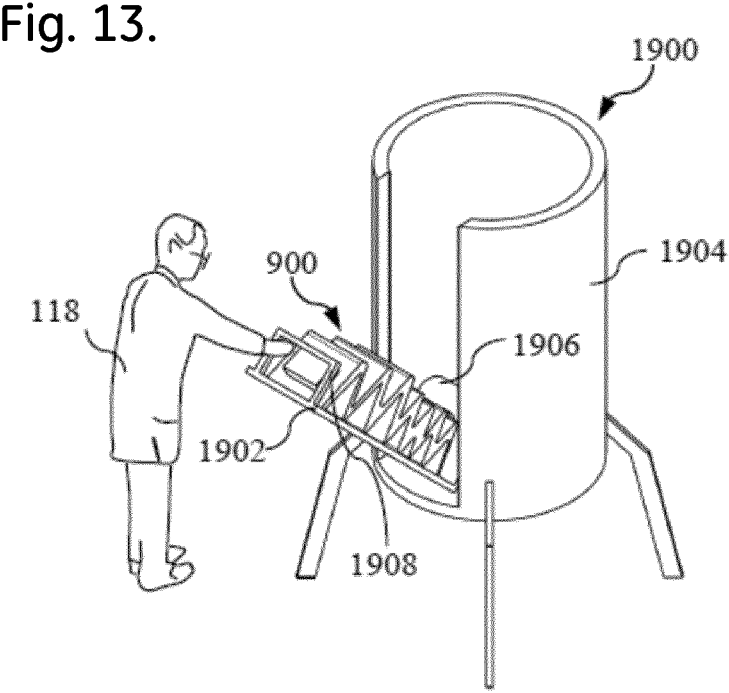
FIG. 14 illustrates a support housing for holding a flexible bioprocess bag according to an embodiment.

In an embodiment, the supporting part for loading the flexible bioprocess bag may not be tilted to form a table configuration—instead it may tilted only till a certain angle with respect to a horizontal plane as shown in FIG. 14. FIG. 14 illustrates a support housing 1900 (hereinafter referred to as housing 1900) having a first segment 1902 (i.e. the supporting part) that is operably connected to a second segment 1904. The first segment 1902 is tilted to a certain angle to open the housing 1900. The flexible bioprocess bag 902 can be loaded on the first segment 1902 by connecting the first end portion 906 to a base segment 1906 and connecting the second end portion 908 to a retainer 1908. Here, the first segment 1902 may have a wider profile for holding the flexible bioprocess bag 902. The retainer 1908 may be similar to the retainer 1308 described with respect to FIG. 8a even though not illustrated in FIG. 14. Therefore, the retainer 1908 can move on a track configured in an inner portion of the first segment 1902. While connecting the second end portion 908, retainer 1908 may move closer to the base segment 1906. Then, after connecting the second end portion 908 to the retainer 1908, the retainer 1908 can move to the top end portion of the first segment 1902. The retainer 1908 stretches-out the flexible bioprocess bag 902 while moving. The movement of the retainer 1908 can be controlled manually by the operator 118 or may be controlled by a control unit such as the control unit 138. In another embodiment, the first segment 1902 may not have the retainer 1908 but can be any receiver that can connect to the second end portion 908 of the flexible bioprocess bag 902 and move along the first segment 1902 to stretch the flexible bioprocess bag 902.

Figure 15:
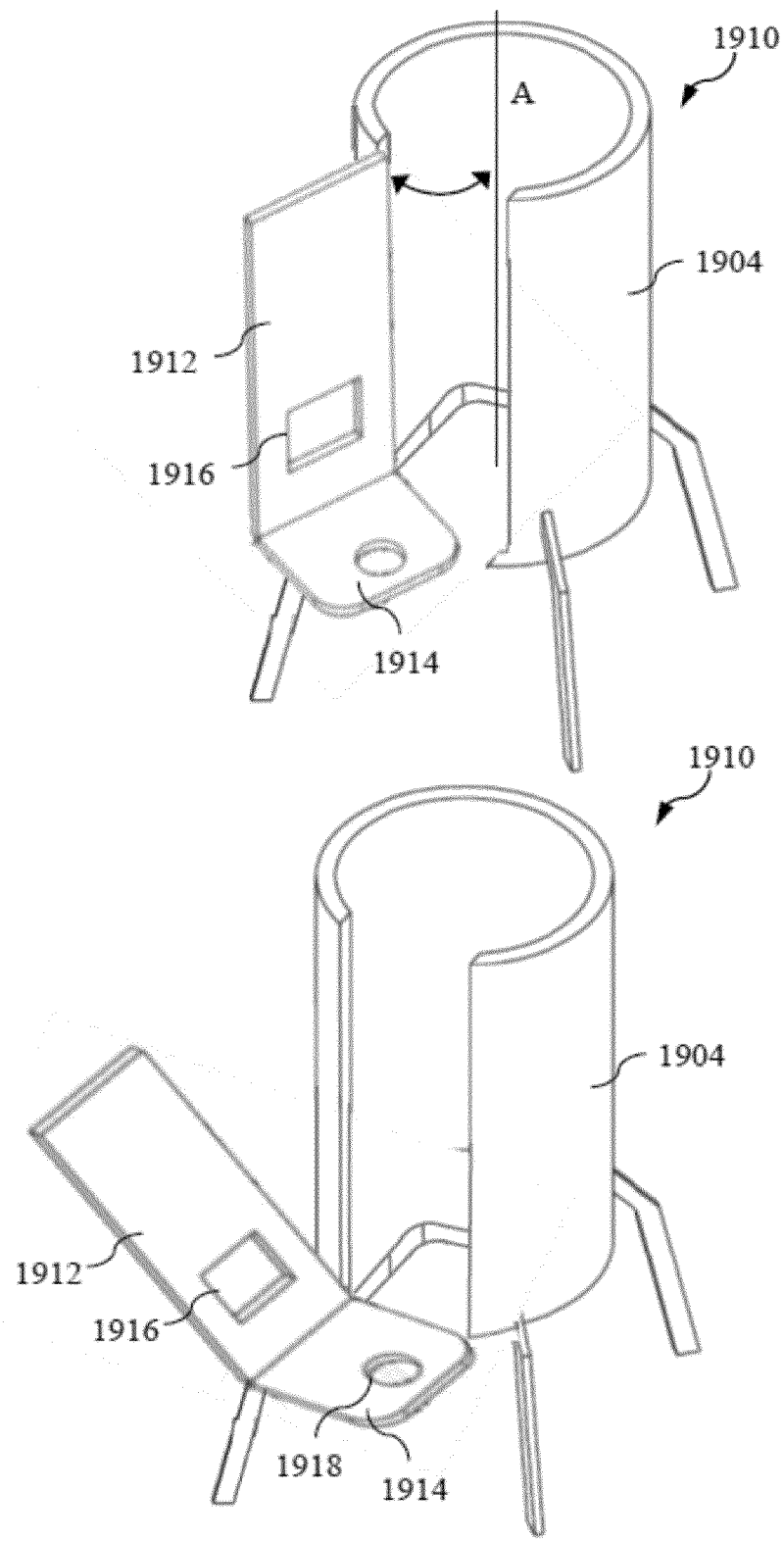
FIG. 15 illustrates a support housing having a first segment (i.e. the supporting part) that is operably connected to the second segment according to an embodiment.

FIG. 15 illustrates a support housing 1910 having a first segment 1912 (i.e. the supporting part) that is operably connected to the second segment 1904 according to an embodiment. A base segment 1914 is connected to the first segment 1912. In an embodiment, the base segment 1914 is operably connected to the first segment 1912. In some embodiments, the base segment 1914 and the first segment 1912 may be part of a single unit and hence they together form the supporting part. The first segment 1912 is rotated at an angle with respect to an axis 'A'. For instance, the first segment 1912 may be rotated at 90° angle to open the housing 1910. Thereafter, the first segment 1912 may be tilted at an angle as shown in FIG. 15 reducing the footprint of the housing 1910. The first segment 1912 may be connected to the second segment 1904 using a rotatable connector or any other connection means that enables the first segment 1912 to rotatably tilt with respect to the second segment 1904. The rotatable connector or the connection means may be located closer to the base segment 1914. Further, there may be locking means in the rotatable connector or any connection means which enables the first segment 1912 to be locked at desired tile angle.

The flexible bioprocess bag can be loaded on the first segment 1912. It may be envisioned that the first segment 1912 may be rotated at different angles other than 90° angle and also tilted at different angles according to various other embodiments. In an embodiment, the first segment 1912 can be oriented parallel to the horizontal plane to form the table configuration even though not illustrated in FIG. 15. An interface retainer 1916 in the first segment 1912 and a mating retainer 1918 in the base segment 1914 facilitate in holding or retaining the flexible bioprocess bag on the first segment 1912. This is explained earlier in detail with respect to earlier figures.

Figure 16:
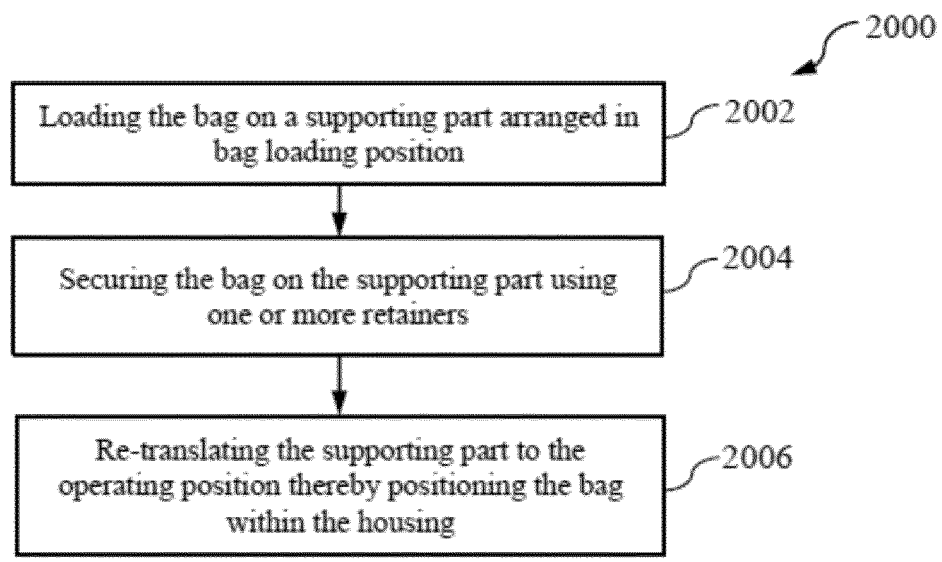
FIG. 16 illustrates a flow diagram of a method of providing a flexible bioprocess bag in a support housing according to an embodiment.

FIG. 16 illustrates a flow diagram of a method 2000 of providing a flexible bioprocess bag in a bioreactor according to an embodiment. The bioreactor includes a support housing (hereinafter referred to as housing) having a sidewall that includes a first segment and a second segment. The first segment is movable in relation to the second segment between an open and closed position. The method 2000 includes loading the flexible bioprocess bag on a supporting part arranged in a bag loading position or in a table configuration at step 2002. The supporting part is translated from an operating position to the bag loading position. The supporting part is aligned parallel to the horizontal plane so that the operator or user can conveniently place the flexible bioprocess bag on the supporting part at the ground level. The flexible bioprocess bag is secured on the flexible bioprocess bag using one or more retainers at step 2004. In an embodiment the housing includes a retainer for securing the flexible bioprocess bag on the supporting part. Once the flexible bioprocess bag is securely loaded, the supporting part is re-translated to an operating position thereby positioning the flexible bioprocess bag within the housing at step 2006.

Figure 17:
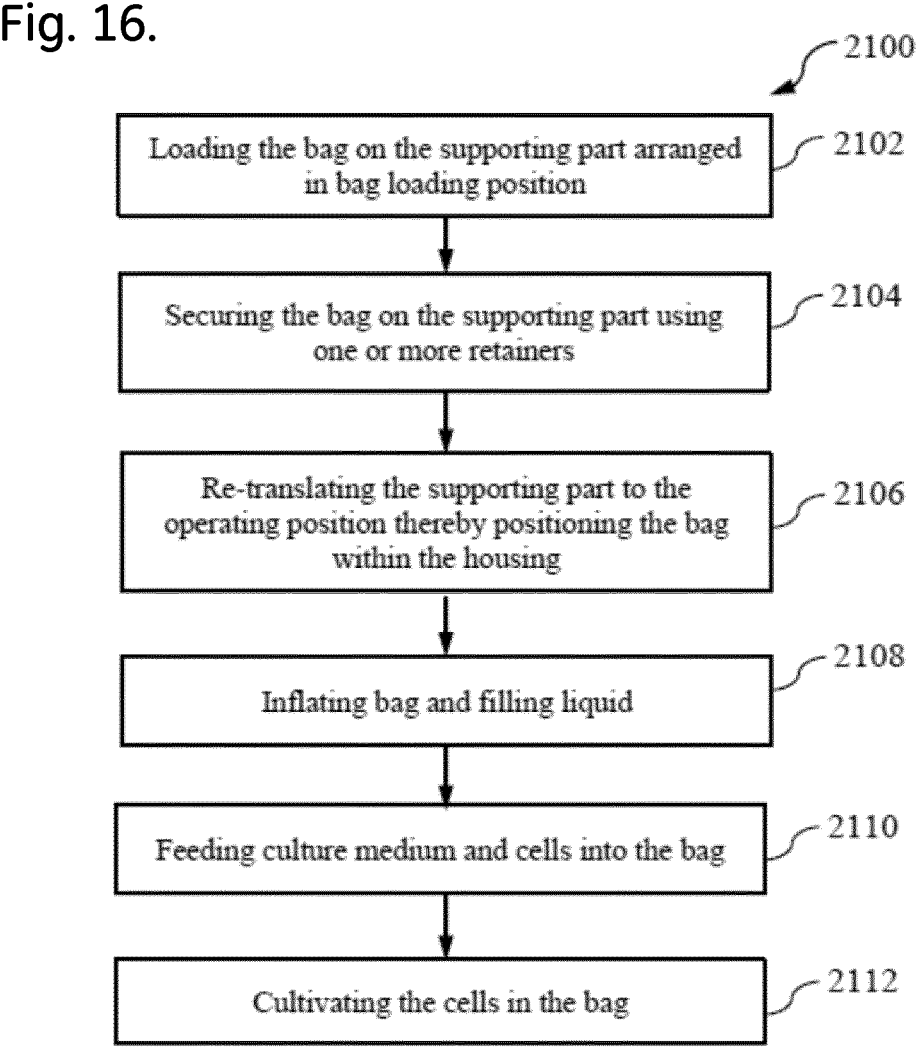
FIG. 17 illustrates a method for cultivating cells in a flexible bioprocess bag arranged in a support housing according to an exemplary embodiment.

Turning now to FIG. 17 illustrating a flow diagram of a method 2100 for cultivating cells in a bioreactor. The bioreactor includes a support housing (hereinafter referred to as housing) that can hold and mix fluids and contents for cultivating cells. A supporting part of the housing is translated from the operating position to a bag loading position. The supporting part can be aligned with the horizontal plane so that it is configured as the bag loading support surface. The flexible bioprocess bag is then loaded on the supporting part at step 2102. The flexible bioprocess bag is secured on the supporting part using one or more retainers at step 2104. For loading the flexible bioprocess bag, a portion of the base i.e., base segment is moved towards a vertical plane. A bottom portion of the flexible bioprocess bag is connected to the base segment. The flexible bioprocess bag includes a mixing unit arranged at the bottom portion which can connect to a drive unit configured at the base segment. The drive unit is capable of driving the mixing unit.

Once loaded, the supporting part is re-translated to the operating position thereby positioning the flexible bioprocess bag within the housing at step 2106. The base segment and the retainers help in orienting the flexible bioprocess bag in the vertical orientation. The bag interface plate connected to an opening in the supporting part helps in the radial orientation of the flexible bioprocess bag along at least one side wall in the housing when in vertical orientation. Once loaded and brought into the vertical orientation, the flexible bioprocess bag can be inflated and filled with liquid at step 2108. Inflation of the flexible bioprocess bag with air and the filling with liquid for processing are typically executed as two subsequent steps. For the step of filling the flexible bioprocess bag with liquid, the housing will be closed. In one embodiment, partial inflation or filling of the flexible bioprocess bag with air and/or liquid can be performed while the housing and the supporting part are not completely closed. The partial inflation and/or filling can help in a stepwise inflation of the flexible bioprocess bag in the scope of assuming the final shape for operation at operating liquid volume.

During inflation, the flexible bioprocess bag may inflate in a substantially radial direction and manner given that retainers at top portion (e.g. a first end portion) and bottom portion (e.g. a second end portion) of the flexible bioprocess bag secure the flexible bioprocess bag in a stretched out alignment along the central axis of the flexible bioprocess bag arranged in the operating position or vertical orientation.

In order to assist a controlled inflation of the flexible bioprocess bag and thereby achieving a correct sequence and progress in the inflation process as well as the flexible bioprocess bag assuming its correct final shape, the bag and its film sheets may be fitted in one embodiment with retainers such as, Velcro tape, snap fit members, securing belts and so on that are released in a stepwise manner during inflation. In another embodiment, the flexible bioprocess bag and film may be restricted during deflation after processing by securing belts or similar that help the deflating flexible bioprocess bag to assume a shape that allows the tilting of supporting part with the deflated flexible bioprocess bag such that the integrity of the flexible bioprocess bag is not compromised and/or the flexible bioprocess bag is within the inner surface of the supporting part.

The flexible bioprocess bag is connected to multiple feed tubes that are capable of feeding culture medium and cells into the flexible bioprocess bag at step 2108. In addition to culture medium and cells, other contents such as, buffer, base, oxygen and other gases may be also fed into the flexible bioprocess bag at step 2110. The mixing unit is used to mix the contents filled in the flexible bioprocess bag. The mixing process enables contents to be mixed properly so that the cells can be cultivated properly at step 2112. It is critical to control the mixing unit mixing speed and other parameters which determines how effectively the oxygen can be supplied to cells and avoid any cell damage.

Figure 18:
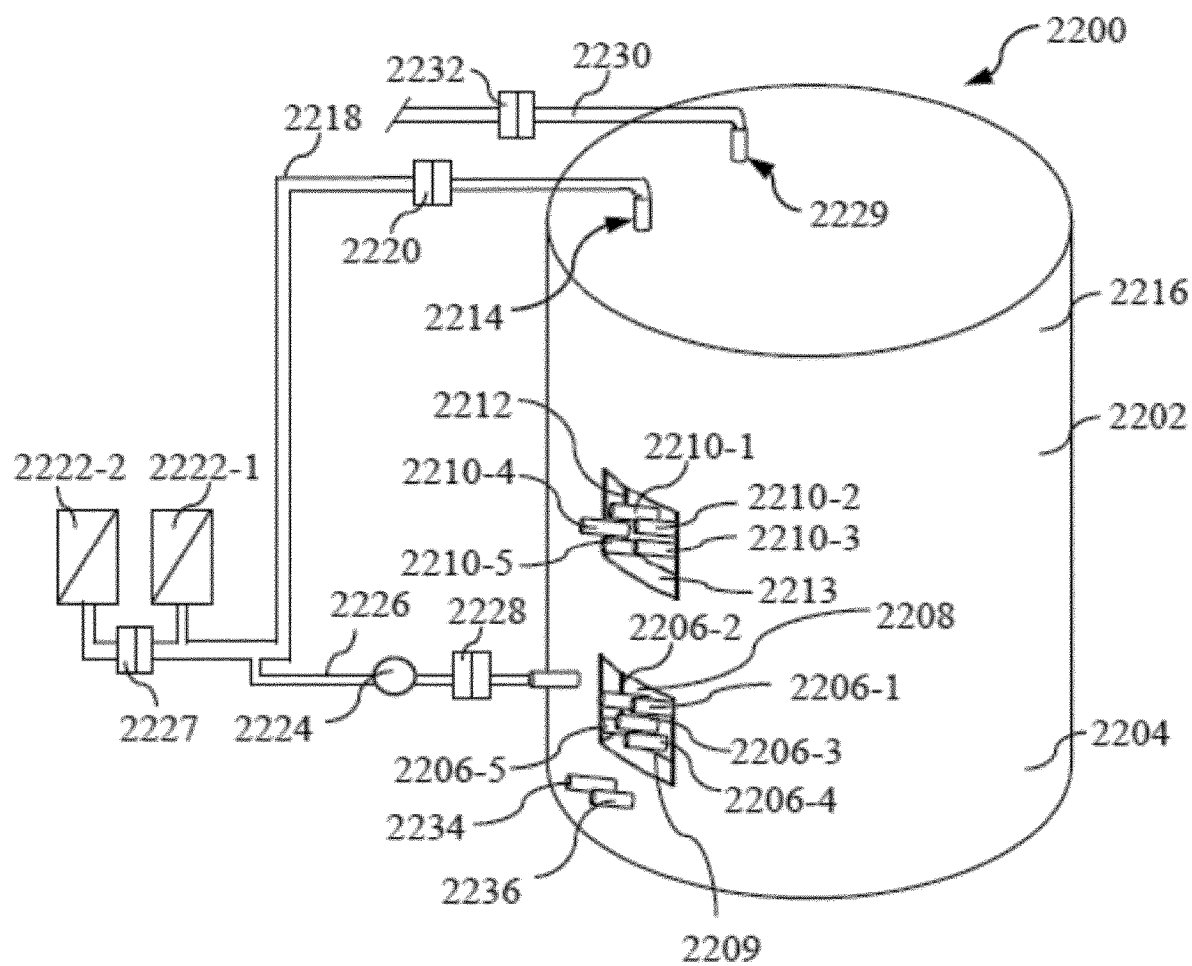
FIG. 18 illustrates an exemplary flexible bioprocess bag according to an embodiment.

FIG. 18 illustrates a flexible bioprocess bag 2200 according to an embodiment. The flexible bioprocess bag 2200 includes one or more walls such as, a wall 2202 that form an interior of the flexible bioprocess bag 2200. In an embodiment, an inner wall defines the interior of the flexible bioprocess bag 2200. The flexible bioprocess bag 2200 includes one or more fluid ports at an end portion 2204 (i.e. first end portion) of the wall 2202. The one or more fluid ports for example, fluid ports 2206-1, 2206-2, 2206-3, 2206-4 and 2206-5, may be held by a first interface plate 2208. The first interface plate 2208 may be held in a holding means 2209. In an embodiment, the first interface plate 2208 may have the fluid ports 2206-1, 2206-2, 2206-3, 2206-4 and 2206-5 as its integral part. In another embodiment, the first interface plate 2208 may be modular and accordingly it can arrange or add or reduce fluid ports based on the requirement of the operator. Moreover, the fluid ports can also be arranged in the first interface plate 2208 in a different manner. For instance, all fluid ports may be arranged in a line. Alternatively, the fluid ports may be arranged in a different configuration in the first interface plate 2208.

The flexible bioprocess bag 2200 may include one or more sensor ports such as, sensor ports 2210-1, 2210-2, 2210-3, 2210-4 and 2210-5 held in a second interface plate 2212. The second interface plate 2212 may be positioned at a portion substantially proximal to the end portion 2204 of the flexible bioprocess bag 2200. The second interface plate 2212 is held by a holding means 2213. In an embodiment, the second interface plate 2212 may have the sensor ports 2210-1, 2210-2, 2210-3, 2210-4 and 2210-5 as its integral part. In another embodiment, the second interface plate 2212 may be modular and accordingly it can arrange or add or reduce sensor ports based on the requirement of the operator. Moreover, the sensor ports can also be arranged in the second interface plate 2212 in a different manner. For instance, all sensor ports may be arranged in a line. Alternatively, the sensor ports may be arranged in a different configuration in the second interface plate 2212.

In an alternate embodiment, the flexible bioprocess bag 2200 may have only one of the first interface plate 2208 and the second interface plate 2212 holding respective fluid ports and sensor ports.

The flexible bioprocess bag 2200 may have an exhaust outlet 2214 at an end portion 2216 (i.e. second end portion). An exhaust tube 2218 is connected to the exhaust outlet 2214 by the operator. A connector 2220 connects the exhaust tube 2218 to the exhaust outlet 2214. During operation, various exhaust gases are expelled through the exhaust outlet 2214 and then passes out through the exhaust tube 2218. The exhaust gases may need to be filtered when passed out to the atmosphere. The operator may connect one or more filters such as, a filter 2222-1 and a filter 2222-2 to the exhaust outlet 2214 through the exhaust tube 2218. The filter 2222-1 and the filter 2222-2 may be same type of filters or different types of filters. In another embodiment, even though only two filters are shown to be present, however there can be other exhaust filters that act as back-up exhaust filters which can function when the filters 2222-1 and 2222-2 are blocked. These filters are positioned such that it is easily accessible for the operator standing on the floor. The filter 2222-2 can be connected to the tube 2226 through a connector 2227. This provides an advantage of performing ground level operation by the operator. Condensation can occur within the tube 2218, and therefore a pump 2224 may be used to pump back the condensate into the flexible bioprocess bag 2200 through a tube 2226. The tube 2226 is connected to the flexible bioprocess bag 2200 through a connector 2228. Further while performing operation in the flexible bioprocess bag 2200, there may be a need for gas (e.g. overlay gas) to be supplied to the ingredients or contents of the flexible bioprocess bag 2200. This overlay gas may need to supplied through a gas port 2229 arranged at the end portion 2216 of the wall 2202. A gas tube 2230 is connected to the gas port 2229 through a connector 2232.

Connectors for connecting components or tubing in fluid contact with the mixing unit, which are connected external and adjacent to the flexible bioprocess bag 2200, like the shown exemplary connectors 2220 and 2227, may be provided in different configurations. The components external and adjacent to the flexible bioprocess bag 2200 typically comprise liquid addition or removal lines, gas addition and exhaust gas removal lines, sensors, mixing elements, sparging elements etc. and may come with different sizes, shapes and diameters in the connection to the flexible bioprocess bag. One configuration for a connection is of fixed type, for example tubing port welded into the wall of the flexible bioprocess bag 2200, the tubing port providing a barb connection for attaching the tubing. Similar fixed connections may be provided for attaching sensors etc., to the flexible bioprocess bag. Components attached to the flexible bioprocess bag using fixed type connections are typically pre-sterilized together with the flexible bioprocess bag. Another type of connection provides an aseptic connection feature, hereby allowing two separate pre-sterilized components to be connected at the point of use while maintaining the sterility in the internal volume of these components. Aseptic connectors that allow for a connection in different sizes are provided by GE Healthcare™ (e.g., ReadyMate™ Connectors), for example. The use of aseptic connections allows for handling and installing components of the mixing unit and bioreactor in subsequent steps, hereby reducing the size, complexity and weight of components during the installation steps and thereby enhancing ergonomics and ease of use. The modularity provided by the use of aseptic connectors increases also the flexibility in combining different components with different properties depending on the specific application needs. Further, the modularity allows for increased flexibility in packaging, storage and transport of the components. Aseptic connections may be applied adjacent to the walls of the flexible bioprocess bag or in tubing sections along the length of tubing. In another embodiment, the mixing unit and flexible bioprocess bag are provided with aseptic disconnectors that allow for a disassembly of the mixing unit during processing and in particular after processing when removing the flexible bioprocess bag from the vessel. Aseptic disconnectors facilitate a closed system approach during assembly and can protect the operator and environment from exposure to fluids internal to the mixing unit and flexible bioprocess bag.

The flexible bioprocess bag 2200 may have a gas sparging unit 2234 (also called a sparger) arranged at a bottom portion (i.e. at the end portion 2204) of the wall 2202. The gas sparging unit 2234 supplies gas into the flexible bioprocess bag 2200. The gas is utilized by the ingredients or contents in the flexible bioprocess bag 2200. The function of the gas sparging unit 2234 is explained earlier.

The flexible bioprocess bag 2200 includes a drain port 2236 for draining the contents from the flexible bioprocess bag 2200. The contents may be ingredients or any matter that are unwanted. Drain port 2236 is preferably allowing full drainability of the flexible bioprocess bag and reactor volume and the opening of the drain port 2236 at the internal of the flexible bioprocess bag are therefore positioned at a lowest point in the flexible bioprocess bag 2200. For example, during a bioprocess operation or mixing process there may be ingredients that are formed and may be unwanted which needs to be drained through the drain port 2236. Alternatively, the contents from the flexible bioprocess bag 2200 may be drained out using the drain port 2236 for emptying and subsequent optional rinsing or flushing of the flexible bioprocess bag 2200. In an alternate embodiment, the tube 2226 can be connected to one of the drain port 2236 and the gas sparging unit 2234.

The flexible bioprocess bag 2200 may be loaded in a housing similar to any of the housings described in FIGS. 1a-h and FIG. 2. After the flexible bioprocess bag 2200 is inflated the tubes 2230, 2218 and 2226 can be connected to respective connectors 2232, 2220, 2228 and 2227 provided in the flexible bioprocess bag 2200. Alternatively, the flexible bioprocess bag 2200 may be a standalone unit for holding solutions or fluids or ingredients or contents.

Figure 22:
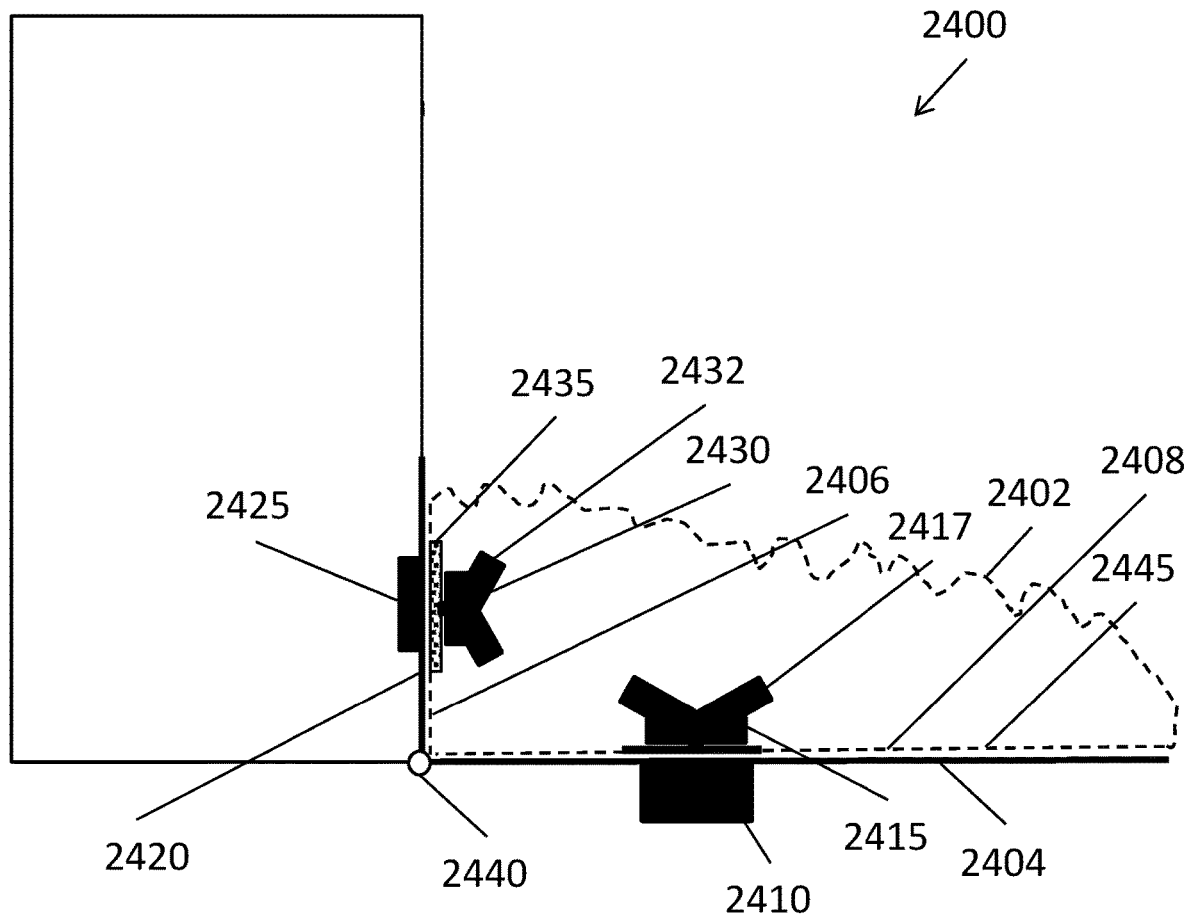
FIG. 22 illustrates a flexible bioprocess bag with first and second mixing units, during mounting in a support housing with first and second drive units, according to certain embodiments.

In some embodiments of the support housing 2400 for the bioprocess bag 2402 disclosed above, illustrated in FIG. 22, the first segment 2404 comprises a first drive unit 2410 for connecting and driving a first mixing unit 2415 in the flexible bioprocess bag. This drive unit can suitably be a magnetic drive unit. Further, the base segment 2420 or the side wall may comprise a second drive unit 2425 (e.g. a magnetic drive unit) for connecting to a second mixing unit 2430 in the flexible bioprocess bag. The base segment or side wall may also comprise a mating gas supply retainer (not shown in FIG. 22) adjacent to the second drive unit for connecting to a sparger 2435 in the flexible bioprocess bag, adjacent to the second mixing unit. In FIG. 22, the first segment 2404 and the base segment 2420 are shown as being tiltable around a horizontal axis 2440.

In some embodiments of the above method of providing a flexible bioprocess bag 2402 in a bioreactor, the first segment 2404 may likewise comprise a first drive unit 2410 for connecting and driving a first mixing unit 2415 in the flexible bioprocess bag. This drive unit can suitably be a magnetic drive unit. Further, the base segment 2420 or the side wall may comprise a second drive unit 2425 (e.g. a magnetic drive unit) for connecting to a second mixing unit 2430 in the flexible bioprocess bag. The base segment or side wall may also comprise a mating gas supply retainer (not shown) adjacent to the second drive unit for connecting to a sparger 2435 in the flexible bioprocess bag, adjacent to the second mixing unit.

Figure 21:
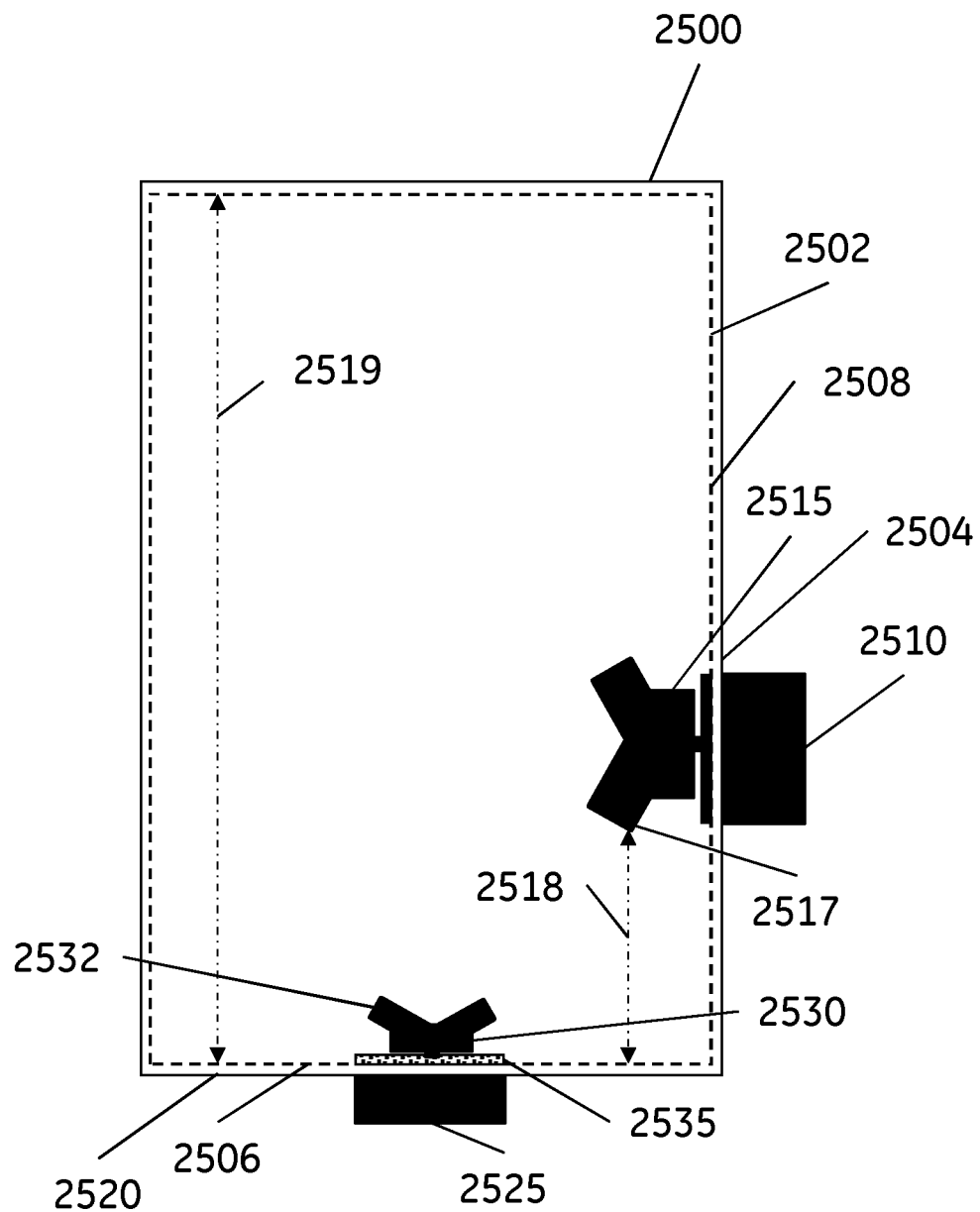
FIG. 21 illustrates a flexible bioprocess bag with first and second mixing units, mounted in a support housing with first and second drive units, according to certain embodiments.
Figure 23:
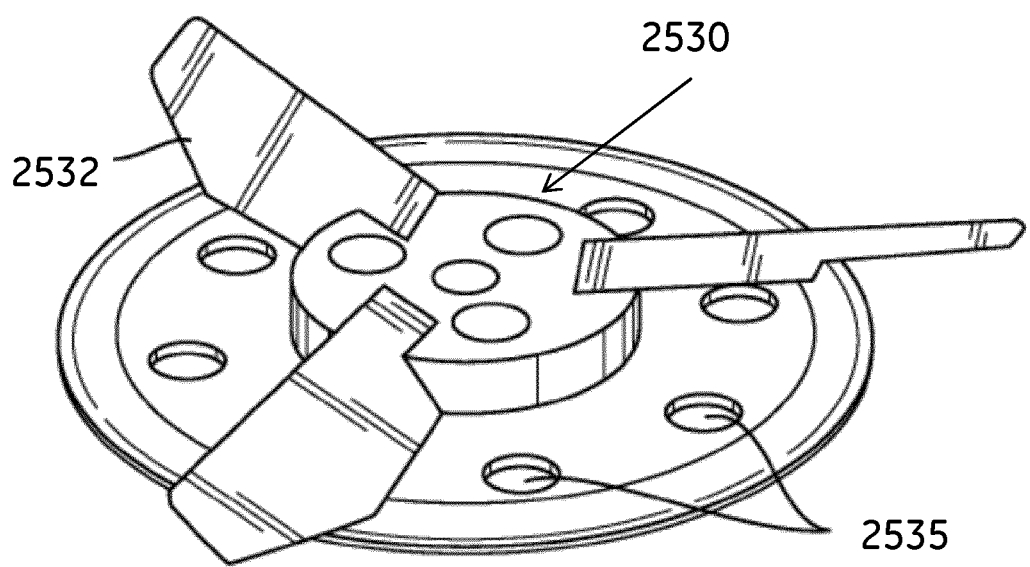
FIG. 23 illustrates a sparging unit with a second mixing unit according to certain embodiments.

In certain embodiments of the flexible bioprocess bag 2402; 2502 as disclosed above, illustrated in FIGS. 21 and 22, a side wall 2445; 2508 of the flexible bioprocess bag comprises a first mixing unit 2415; 2515 configured to be connected to a first drive unit 2410; 2510 in said supporting part 2404. The bag may further comprise a sparging unit 2435; 2535 attachable to a mating gas supply retainer (not shown) provided at a portion of the support housing. It may also comprise a second mixing unit 2430; 2530 configured to be connected to a second drive unit 2425; 2525 of the support housing. Suitably, the sparging unit and the second mixing unit can be provided adjacent to each other in the flexible bioprocess bag, e.g. as illustrated in FIG. 23.

Figure 19:
FIG. 19 illustrates computerized fluid dynamics (CFD) simulations of mixing in a vessel with a), c), e) a bottom-mounted impeller and b), d), f) a side wall-mounted impeller.
Figure 19:
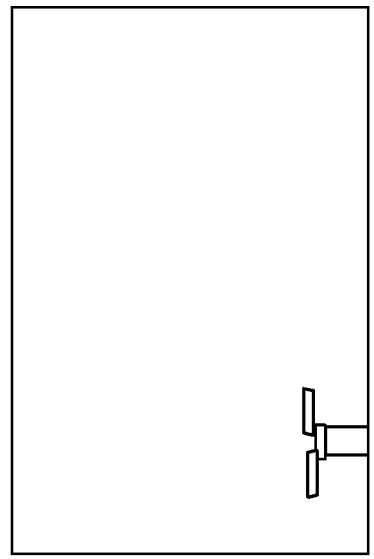
Figure 19:
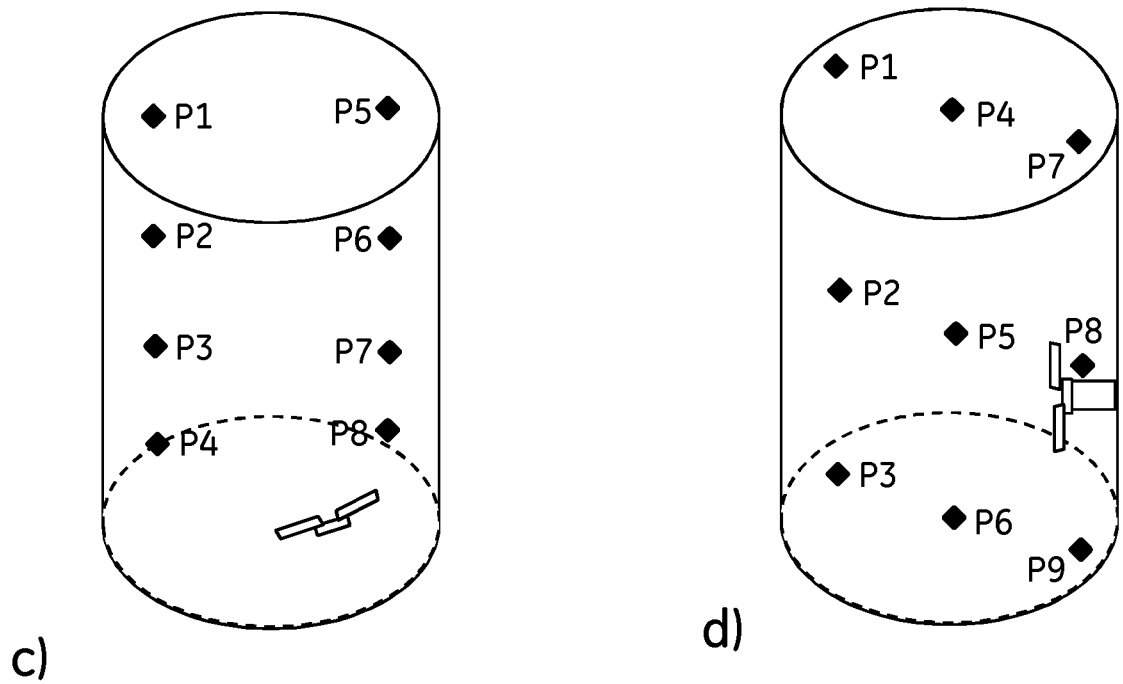
Figure 19:
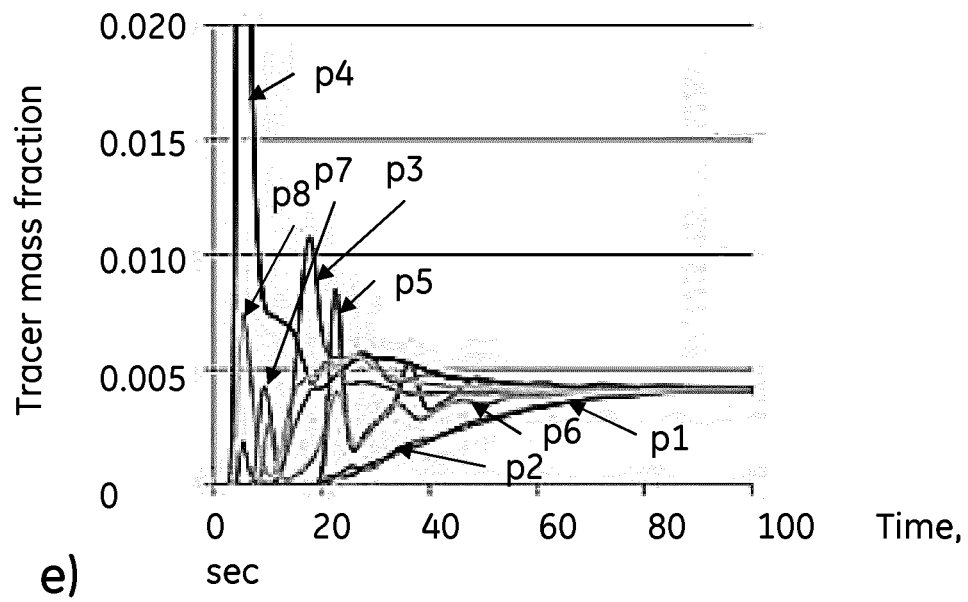
Figure 19:
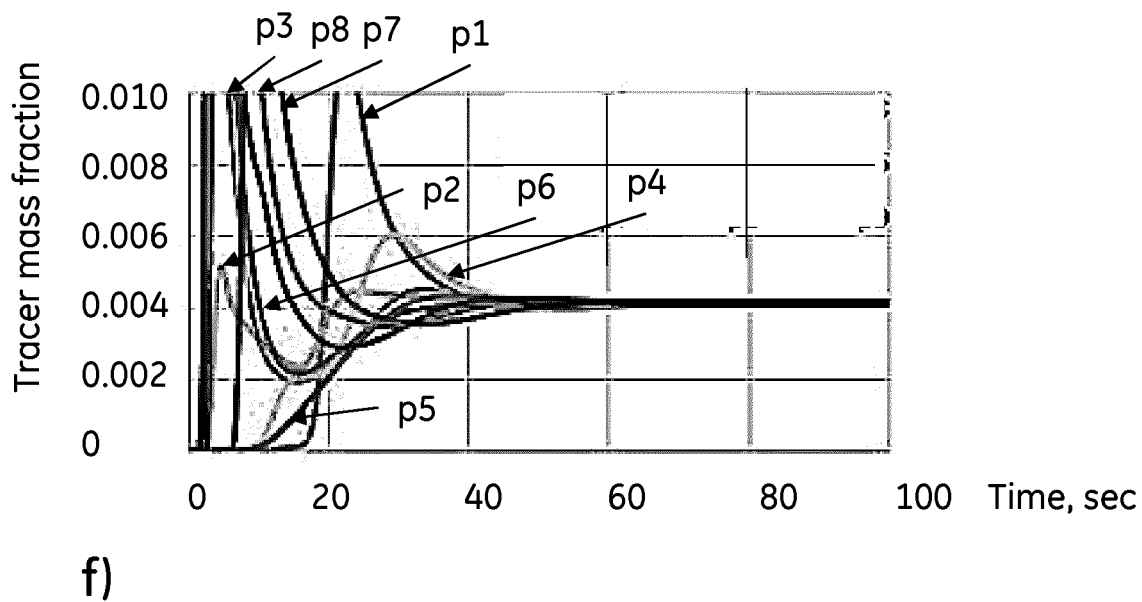
Figure 20:
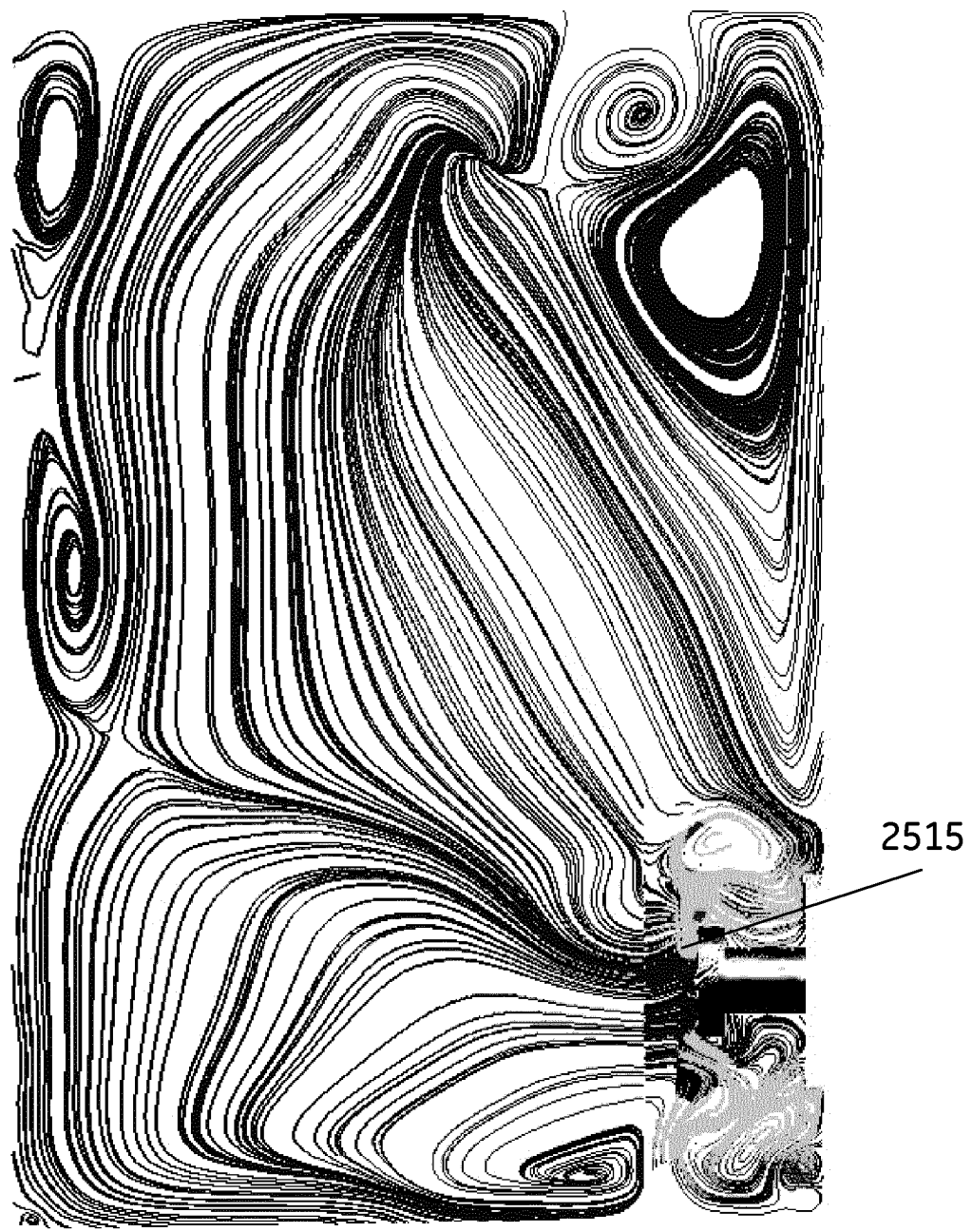
FIG. 20 illustrates the flow pattern from the CFD simulation of the side wall-mounted impeller of FIG. 19b), d) and f).

In a further aspect, the invention discloses a flexible bioprocess bag 2402; 2502 comprising a first mixing unit 2415; 2515 configured for agitating a content of the flexible bioprocess bag and a second mixing unit 2430; 2530, adjacent to a sparging unit 2435; 2535, and configured for controlling the size and distribution of bubbles emanating from the sparging unit. One or both of the first and second mixing units can suitably be magnetically driven. The first mixing unit may e.g. be provided on a side wall 2408; 2508 of the flexible bioprocess bag. The second mixing unit and the sparging unit may e.g. be provided on a bottom wall 2406; 2506 of the flexible bioprocess bag. Suitably the first mixing unit has an impeller 2417; 2517 which is located away from the bottom wall of the flexible bioprocess bag, which is advantageous for bulk mixing of the fluid in the bag. The impeller may e.g. be located at a distance 2518 of at least 5%, or at least 10%, of the inner height 2519 of the flexible bioprocess bag from the bottom wall 2506. This can apply both for side wall- and bottom-wall mounted mixing units. If the first mixing unit is bottom-mounted (not shown), the impeller then needs to be mounted on a shaft to provide the distance from the bottom. The impeller 2417; 2517 of the first mixing unit can suitably be an axial flow impeller, e.g. a segmented or pitched blade impeller. For the second mixing unit, good bubble dispersion can be achieved with an impeller 2432; 2532 close to the sparging unit, e.g. where the distance from the impeller to the sparging unit is less than 5 cm, such as less than 2 cm or 0.5-1 cm. The impeller 2432; 2532 in the second mixing unit may e.g. be a segmented or pitched blade impeller, as illustrated in FIG. 23. The impeller diameter can suitably be less than 0.5 times the diameter of the bag, such as less than 0.4 times the bag diameter or 0.3-0.4 times the bag diameter. The sparging unit can be shaped as one or more discs, as in FIG. 23, but also other shapes are possible—e.g. porous ring structures. By decoupling the bulk mixing from the bubble dispersion, both processes can be better optimized in comparison to the case where one mixing unit has a double function. The efficiency of a bulk mixing unit, in this case a side wall-mounted axial flow impeller, is illustrated by the CFD simulations of FIGS. 19 and 20. FIG. 19a) shows a reference bottom-mounted impeller in a flat-bottomed 500 L cylindrical vessel, with tracer locations P1 to P8 according to FIG. 19c), giving the mixing time of 60 s (T95— time to 95% mixing homogeneity). In contrast, the side wall impeller of FIG. 19b) and d) gives a mixing time T95 of 38 s. FIG. 20 shows the flow pattern of the side wall-mounted impeller across a central vertical plane of the vessel.

In a yet further aspect, the invention discloses a support housing 2400; 2500 for a flexible bioprocess bag 2402; 2502, comprising a first drive unit 2410; 2510 (e.g. a magnetic drive unit) and a second drive unit 2425; 2525 (e.g. a magnetic drive unit) for connecting and driving a first mixing unit 2415; 2515 and a second mixing unit 2430; 2530 respectively in a flexible bioprocess bag when mounted in said support housing, where the first drive unit may be provided on a side wall 2504 or side wall segment 2404 of the support housing. The second drive unit may e.g. be provided on a bottom wall 2520 or bottom wall segment 2420 of said support housing. The support housing may further comprise a mating gas supply retainer (not shown) adjacent to the second drive unit for connecting to a sparging unit 2435; 2535 in the flexible bioprocess bag, adjacent to the second mixing unit. Suitably, the power of the first drive unit may be at least 2 times the power of the second drive unit, such as at least 5 times or at least 10 times the power of said second drive unit. More power is needed for bulk agitation than for bubble dispersion and it can be advantageous to design the system such that the second mixing unit primarily disperses bubble away from the sparger, while the larger first mixing unit provides bulk mixing, including mixing the dispersed bubbles into the bulk fluid.

Figure 24:
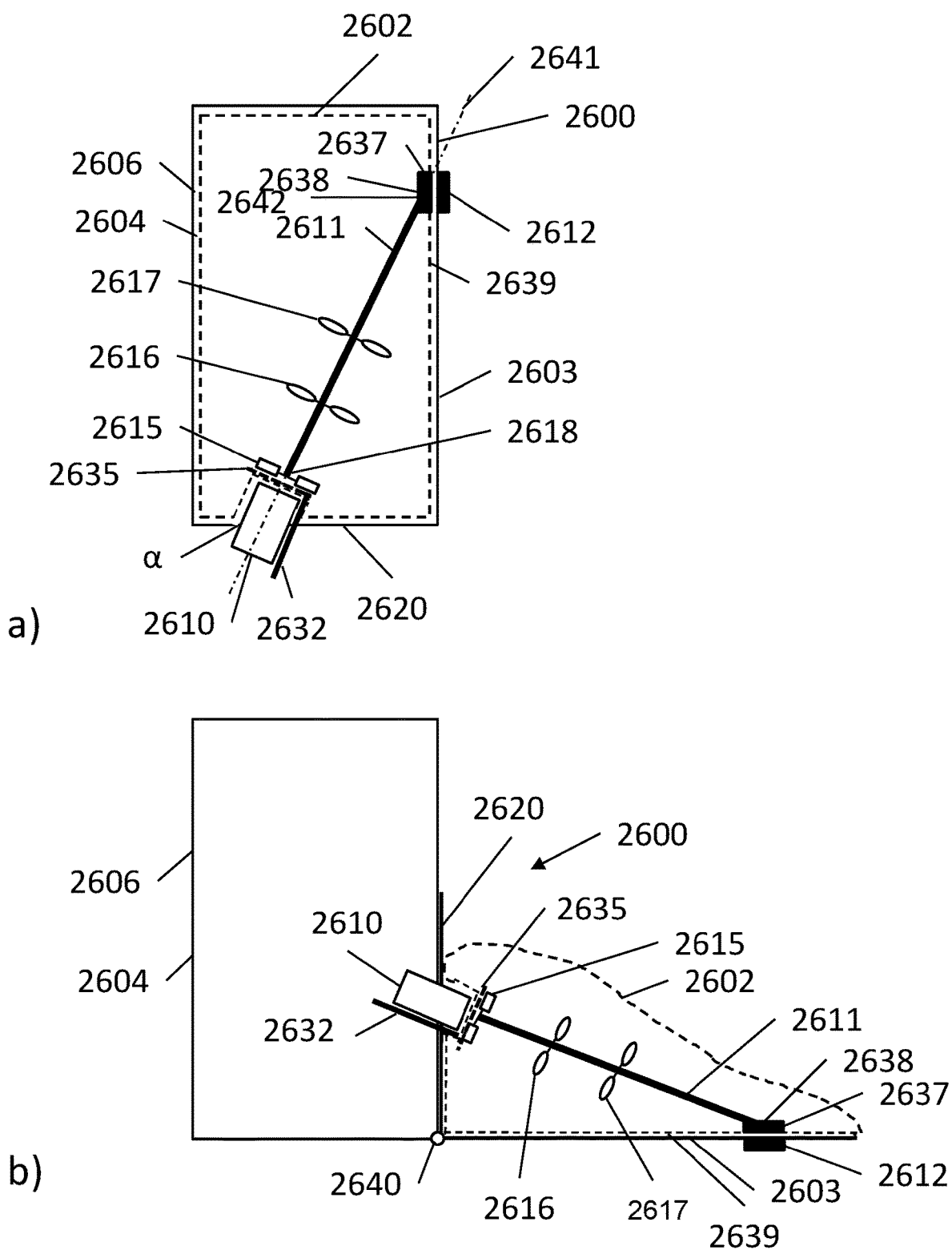
FIG. 24 illustrates a support housing and a flexible bioprocess bag with multiple mixing units mounted on a single shaft. *a*) closed (working) position, *b*) open (loading) position.

In some embodiments, illustrated by FIG. 24a) and b), the invention discloses a support housing 2600 for a flexible bioprocess bag 2602, comprising a drive unit 2610 having an acute angle α relative to a base segment 2620 of said support housing. The drive unit is arranged for connecting and driving a shaft 2611 with a plurality of mixing units 2615, 2616, 2617 in the flexible bioprocess bag. This drive unit can suitably be a magnetic drive unit and is suitably arranged in base segment 2620 or in a recess of the base segment. As described above, a first segment 2603 of a side wall 2604 and the base segment 2620 are tiltable relative to a second segment 2606 of the side wall, suitably around a horizontal axis 2640. The base segment may also comprise a mating gas supply retainer 2632 adjacent to the drive unit for connecting to a sparger 2635 in the flexible bioprocess bag. First segment 2603 may further comprise a bearing retainer 2612, arranged to engage or interact with a bearing 2638 or bearing holder 2637 on a side wall 2639 of the flexible bioprocess bag, such that a shaft 2611 with a plurality of mixing units in a bag 2602 is rotatably supported at a distal end by the bearing and/or bearing holder and at a proximal end by the drive unit.

The invention further discloses a flexible bioprocess bag 2602, comprising a shaft 2611 with a plurality of mixing units 2615, 2616, 2617 configured for agitating a content of the flexible bioprocess bag. The shaft is arranged to be driven by the drive unit 2610 in the support housing 2600 and, if the drive unit is a magnetic drive unit, the shaft may suitably comprise a set of magnets arranged to couple with a set of permanent magnets or electromagnets in the drive unit. The shaft can suitably be aligned with the drive unit along a common axis of rotation 2641, having an acute angle α in relation to base segment 2620. α may e.g. be in the range of 50-80 degrees, such as 55-75 degrees. A distal end 2642 of shaft 2611 may be rotatably attached to a side wall 2639 of the flexible bioprocess bag, e.g. by a bearing 2638. The bearing 2638 may be directly attached to side wall 2639, or it may be attached via a bearing holder 2637, which can e.g. be a rigid plastic structure welded to the side wall of the bag. The bearing holder, or the bearing, may engage a bearing retainer 2632 on the first segment 2603 of the support housing side wall. It is also contemplated that the bearing holder and the bearing retainer may comprise magnets, allowing magnetic coupling to fix the bearing holder in a correct position. If the side wall of the support housing is perpendicular to the base of the housing, the angle between the side wall and the shaft will be 90 degrees—α, such that this angle may e.g. be in the range of 10-40 degrees, such as 15-35 degrees. The mixing units can comprise a first mixing unit 2615, a second mixing unit 2616 and optionally a third mixing unit 2617. The first mixing unit 2615 can be located at a proximal end 2618 of the shaft, close to the drive unit and sparger 2635. The first mixing unit can then be designed for efficient dispersion of air/gas bubbles from the sparger into the content of the bag. For this purpose, the first mixing unit can e.g. be a radial mixing unit such as e.g. a Rushton turbine. The second and optional third mixing units can be designed for mixing of the bag content and can e.g. be angled blade (e.g. propeller) agitators to provide for axial mixing.

Figure 25:
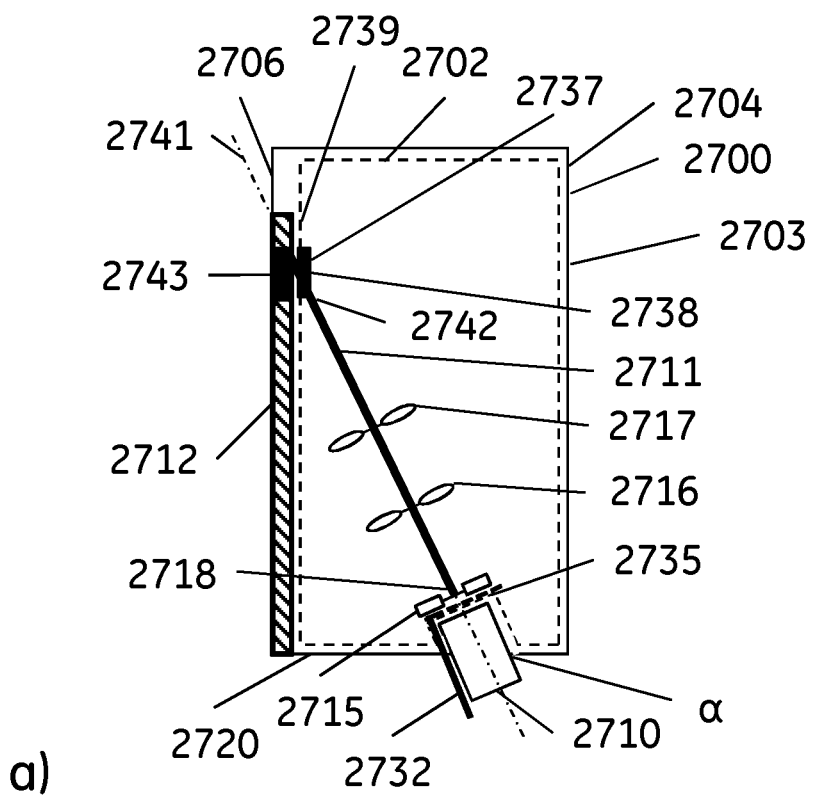
FIG. 25 illustrates a support housing and a flexible bioprocess bag with multiple mixing units mounted on a single shaft. *a*) closed (working) position, *b*) open (loading) position.
Figure 25:
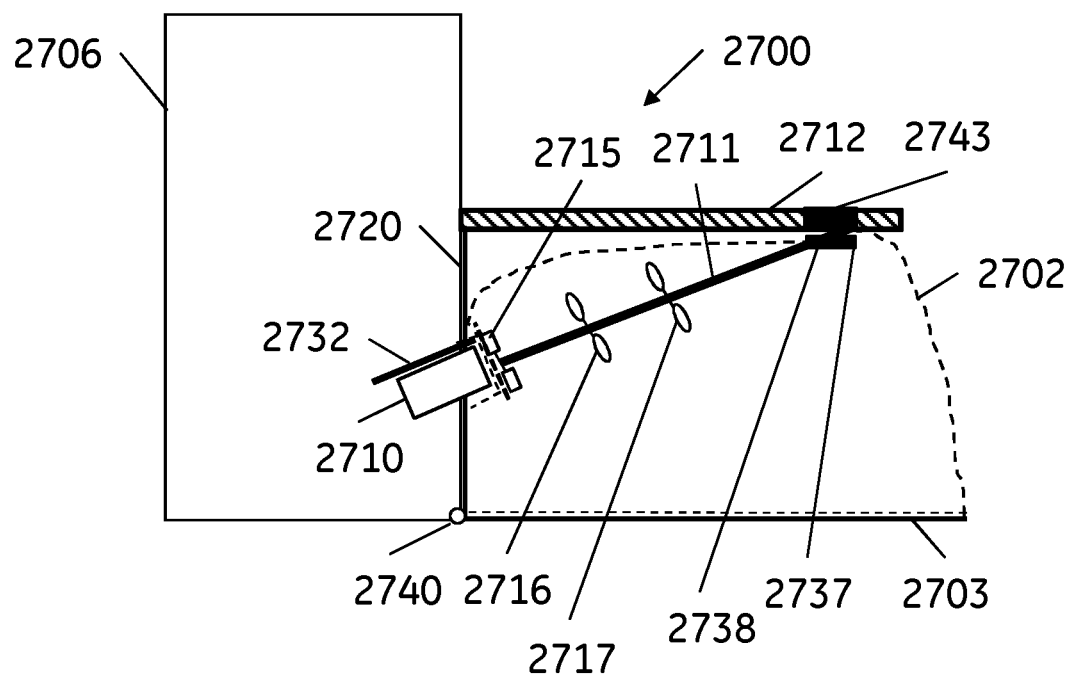

In certain embodiments, illustrated by FIG. 25a) and b), the invention discloses a support housing 2700 for a flexible bioprocess bag 2702, comprising a drive unit 2710 having an acute angle α relative to a base segment 2720 of said support housing. The drive unit is arranged for connecting and driving a shaft 2711 with a plurality of mixing units 2715, 2716, 2717 in the flexible bioprocess bag. This drive unit can suitably be a magnetic drive unit and is suitably arranged in base segment 2720 or in a recess of the base segment. The base segment may also comprise a mating gas supply retainer 2732 adjacent to the drive unit for connecting to a sparger 2735 in the flexible bioprocess bag. As described above, a first segment 2703 of a side wall 2704 and the base segment 2720 are tiltable relative to a second segment 2706 of the side wall, suitably around a horizontal axis 2740. In addition, a baffle or shaft holder rod 2712 on the side wall opposite first segment 2703 is tiltable along with base segment 2720. A bearing retainer 2743 located on or integral with baffle or shaft holder rod 2712 is arranged to engage or interact with a bearing 2738 or bearing holder 2737 on a side wall 2739 of the flexible bioprocess bag, such that a shaft 2711 with a plurality of mixing units in bag 2702 is rotatably supported at a distal end by the bearing and/or bearing holder and at a proximal end by the drive unit.

The invention further discloses a flexible bioprocess bag 2702, comprising a shaft 2711 with a plurality of mixing units 2715, 2716, 2717 configured for agitating a content of the flexible bioprocess bag. The shaft is arranged to be driven by the drive unit 2710 in the support housing 2700 and, if the drive unit is a magnetic drive unit, the shaft may suitably comprise a set of magnets arranged to couple with a set of permanent magnets or electromagnets in the drive unit. The shaft can suitably be aligned with the drive unit along a common axis of rotation 2741, having an acute angle α in relation to base segment 2720. α may e.g. be in the range of 50-80 degrees, such as 55-75 degrees. A distal end 2742 of shaft 2711 may be rotatably attached to a side wall 2739 of the flexible bioprocess bag, e.g. by a bearing 2738. The bearing 2738 may be directly attached to side wall 2739, or it may be attached via a bearing holder 2737, which can e.g. be a rigid plastic structure welded to the side wall of the bag. The bearing holder, or the bearing, may engage a bearing retainer 2743 located on or integral with a baffle or shaft holder rod 2712, opposite the first segment 2703 of the support housing side wall. It is also contemplated that the bearing holder 2737 and the baffle/shaft holder rod 2712 may comprise magnets, allowing magnetic coupling to fix the bearing holder in a correct position. If the side wall of the support housing is perpendicular to the base of the housing, the angle between the side wall and the shaft will be 90 degrees—α, such that this angle may e.g. be in the range of 10-40 degrees, such as 15-35 degrees. The mixing units can comprise a first mixing unit 2715, a second mixing unit 2716 and optionally a third mixing unit 2717. The first mixing unit 2715 can be located at a proximal end 2718 of the shaft, close to the drive unit and sparger 2735. The first mixing unit can then be designed for efficient dispersion of air/gas bubbles from the sparger into the content of the bag. For this purpose, the first mixing unit can e.g. be a radial mixing unit such as e.g. a Rushton turbine. The second and optional third mixing units can be designed for mixing of the bag content and can e.g. be angled blade (e.g. propeller) agitators to provide for axial mixing.

From the foregoing, it will be appreciated that the bioreactor includes a housing that enables a user or operator to load a flexible bioprocess bag in a convenient manner. A supporting part of the housing is movable to be aligned to the horizontal plane attaining a table configuration. Thus, the operator or user can load the flexible bioprocess bag on the supporting part at ground level conveniently. The flexible bioprocess bag can be securely positioned on the supporting part using retainers by the operator. Also, the bioprocess can be connected to multiple feed tubes that are for supplying buffer, culture medium, gases, base and so on to the flexible bioprocess bag at the ground level. The supporting part eliminates the need for the operator to climb up the bioreactor for making connections of feed tubes to the flexible bioprocess bag. As loading of the flexible bioprocess bag happens in the ground level the time required for setting up the bioreactor is reduced, it provides a better user experience.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A support housing, comprising:
   a housing body having a top surface, a bottom wall, and a sidewall extending from the bottom wall to the top surface, an inner region between the top surface, the bottom wall and the sidewall defining an internal volume of the housing body, the sidewall including a first sidewall segment, a second sidewall segment, and a third sidewall segment disposed about the first sidewall segment and the second sidewall segment to support a flexible bioprocess bag, the third sidewall segment having a main wall that receives the flexible bioprocess bag thereon, a base wall perpendicular to the main wall with an opening therein to receive an end portion of the flexible bioprocess bag, the base wall having a surface area that is less than a surface area of the main wall, and one or more retainers to hold the flexible bioprocess bag in place against the main wall and the end portion of the flexible bioprocess bag in the opening of the base wall,
   wherein the first sidewall segment is movable in relation to the second sidewall segment, the first sidewall segment movable between an open position in that the first sidewall segment moves away from the second sidewall segment to provide access to the internal volume of the housing body and a closed position in that the first sidewall segment is aligned with the second sidewall segment to preclude access to the internal volume,
   wherein the third sidewall segment is hingedly connected to the housing body by a hinged mechanism for tiltable translation of the third sidewall segment in relation to the first sidewall segment and the second sidewall segment, the third sidewall segment tiltably translatable at an angle to a longitudinal axis extending through the internal volume of the housing body, the angle of translation of the third sidewall segment extending between a horizontal orientation parallel with a horizontal axis extending away from the bottom wall of the housing body and a vertical orientation parallel with the longitudinal axis, the horizontal orientation defining a loading position for the main wall of the third sidewall segment to receive the flexible bioprocess bag thereon with the end portion of the flexible bioprocess bag in the opening of the base wall of the third sidewall segment, the vertical orientation defining an operation position to operate the flexible bioprocess bag after securing the flexible bioprocess bag to the main wall and the end portion of the flexible bioprocess bag in the opening of the base wall with the one or more retainers and tiltingly translating the third sidewall segment from the horizontal orientation to the vertical orientation, the base wall protruding outward from the main wall to the inner region of the housing body when the third sidewall is in the vertical orientation to form a part of the bottom wall.

2. The support housing of claim 1, wherein the first sidewall segment is tiltably movable in relation to the second sidewall segment.

3. The support housing of claim 1, wherein the third sidewall segment is integral to the first sidewall segment.

4. The support housing of claim 1, wherein the third sidewall segment is translatable at an inclination angle less than 45 degrees above or below a horizontal plane.

5. The support housing of claim 1, wherein the third sidewall segment is translatable to a position less than 150 cm from ground level.

6. The support housing of claim 1, wherein the first sidewall segment is collapsible in a longitudinal direction.

7. The support housing of claim 1, wherein the first sidewall segment is collapsible in a transverse direction.

8. The support housing of claim 1, wherein the third sidewall segment is collapsible in a longitudinal direction.

9. The support housing of claim 1, wherein the third sidewall segment is collapsible in a transverse direction.

10. The support housing of claim 1, wherein a portion of the base wall of the third sidewall segment is movable towards a vertical plane.

11. The support housing of claim 10, wherein the portion of the base wall is movable towards a horizontal plane upon re-translation of the third sidewall segment to the operation operating position.

12. The support housing of claim 1, wherein the flexible bioprocess bag comprises a mixing unit.

13. The support housing of claim 12, wherein the base wall comprises a magnetic drive unit for connecting to the mixing unit in the flexible bioprocess bag.

14. The support housing of claim 1, wherein the base wall or one of the first sidewall segment and the second sidewall segment comprises a mating gas supply retainer adjacent to a second drive unit for connecting to a sparger in the flexible bioprocess bag, adjacent to a second mixing unit.

15. The support housing of claim 1, further comprising a tube management structure for organizing a tube and a connector connected to the flexible bioprocess bag.

16. The support housing of claim 1, wherein the one or more retainers comprises at least one interface retainer provided in the third sidewall segment, wherein the at least one interface retainer is positioned on the third sidewall segment and attachable to an interface plate of the flexible bioprocess bag.

17. The support housing of claim 16, wherein the interface retainer is variable in at least one direction.

18. The support housing of claim 1, further comprising at least one sensor provided in at least one of the third sidewall segment, the first sidewall segment and the second sidewall segment, wherein a sensor of the at least one sensor determines a position of the third sidewall segment and an object adjacent to the support housing.

19. The support housing of claim 1, wherein the one or more retainers comprises a retainer attachable to a mating retaining member of the flexible bioprocess bag.

20. A support housing for a flexible bioprocess bag, the support housing comprising a vertically-oriented cylindrical housing body having a top surface, a bottom wall, and a curved sidewall extending from the bottom wall to the top surface, an inner region between the top surface, the bottom wall and the curved sidewall defining an internal volume of the housing body, the curved sidewall including a first sidewall segment, a second sidewall segment, and a third sidewall segment disposed about the first sidewall segment and the second sidewall segment to support the flexible bioprocess bag, the third sidewall segment having a main wall that receives the flexible bioprocess bag thereon, a base wall perpendicular to the main wall with an opening therein to receive an end portion of the flexible bioprocess bag, the base wall having a surface area that is less than a surface area of the main wall, and one or more retainers to hold the flexible bioprocess bag in place against the main wall and the end portion of the flexible bioprocess bag in the opening of the base wall, wherein the first sidewall segment is movable in relation to the second sidewall segment, the first sidewall segment movable between an open position in that the first sidewall segment moves away from the second sidewall segment to provide access to the internal volume of the housing body and a closed position in that the first sidewall segment is aligned with the second sidewall segment to preclude access to the internal volume, wherein the third sidewall segment is hingedly connected to the housing body by a hinged mechanism for tiltable translation of the third sidewall segment in relation to the first sidewall segment and the second sidewall segment, the third sidewall segment tiltably translatable at an angle to a longitudinal axis extending through the internal volume of the housing body, the angle of translation of the third sidewall segment extending between a horizontal orientation parallel with a horizontal axis extending away from the bottom wall of the housing body and a vertical orientation parallel with the longitudinal axis, the horizontal orientation defining a loading position for the main wall of the third sidewall segment to receive the flexible bioprocess bag thereon with the end portion of the flexible bioprocess bag in the opening of the base wall of the third sidewall segment, the vertical orientation defining an operation position to operate the flexible bioprocess bag after securing the flexible bioprocess bag to the main wall and the end portion of the flexible bioprocess bag in the opening of the base wall with the one or more retainers and tiltingly translating the third sidewall segment from the horizontal orientation to the vertical orientation, the base wall protruding outward from the main wall to the inner region of the housing body when the third sidewall is in the vertical orientation to form a part of the bottom wall.

21. The support housing of claim 20, wherein the first sidewall segment is operably connected to the second sidewall segment.

22. The support housing of claim 20, wherein the third sidewall segment is integral to the first sidewall segment.

23. The support housing of claim 20, wherein the base wall is movable towards a vertical plane.

24. The support housing of claim 23, wherein the base wall is movable towards the vertical plane along with a tiltable translation of the third sidewall segment.

25. The support housing of claim 23, wherein the base wall is movable towards a horizontal plane upon re-translation of the third sidewall segment to the operation position and movement of the first sidewall segment to the closed position.

26. The support housing of claim 23, wherein the flexible bioprocess bag comprises at least one port at a first end portion and a liquid feed port at a second end portion, wherein upon re-translation of the third sidewall segment to the operation position the first end portion of the flexible bioprocess bag is at a top end of the support housing and the second end portion is at the bottom wall of the support housing.

* * * * *